US005656457A

United States Patent [19]

Parkes et al.

[11] Patent Number: 5,656,457

[45] Date of Patent: Aug. 12, 1997

[54] DNA SEQUENCE FOR THE UNIQUE SEQUENCE HERPES SIMPLEX VIRUS TYPE 2-GLYCOPROTEIN G PROTEIN AND METHOD OF EXPRESSING SAID UNIQUE SEQUENCE OF HSV-2GG

[75] Inventors: Deborah Lynn Parkes, Oakland; Stephen Ralph Coates, Orinda, both of Calif.

[73] Assignee: CIBA Corning Diagnostics Corporation, Medfield, Mass.

[21] Appl. No.: 450,360

[22] Filed: May 25, 1995

Related U.S. Application Data

[63] Continuation of Ser. No. 129,021, Sep. 29, 1993, abandoned, which is a continuation of Ser. No. 832,982, Feb. 10, 1992, abandoned, which is a continuation of Ser. No. 351,740, May 12, 1989, abandoned.

[51] Int. Cl.[6] .......................... C12P 21/00; C12N 15/11; C12N 15/38

[52] U.S. Cl. .................... 435/69.3; 435/69.1; 435/172.3; 435/252.31; 435/252.33; 435/254.11; 435/325; 435/348; 435/419; 536/23.72; 536/23.1

[58] Field of Search ................................ 435/69.1, 69.3, 435/70.1, 71.1, 71.2, 172.3, 240.2, 252.31, 252.33, 254.11; 536/23.72, 23.1

[56] References Cited

U.S. PATENT DOCUMENTS

| | | | |
|---|---|---|---|
| 4,452,901 | 6/1984 | Gordon et al. | 436/506 |
| 4,618,578 | 10/1986 | Burke et al. | 435/68 |
| 4,642,333 | 2/1987 | Person | 530/350 |
| 4,661,349 | 4/1987 | Kino et al. | 424/89 |
| 4,709,011 | 11/1987 | Cohen et al. | 530/324 |
| 4,745,182 | 5/1988 | Cohen et al. | 530/387 |
| 4,761,470 | 8/1988 | Emini et al. | 530/326 |
| 4,762,708 | 8/1988 | Cohen et al. | 424/89 |
| 4,764,459 | 8/1988 | Hampar et al. | 435/5 |
| 4,855,224 | 8/1989 | Berman et al. | 435/5 |
| 5,124,255 | 6/1992 | Bolling et al. | 435/69.3 |

FOREIGN PATENT DOCUMENTS

| | | |
|---|---|---|
| 0139417 | 5/1985 | European Pat. Off. . |
| 0263025 | 4/1988 | European Pat. Off. . |

OTHER PUBLICATIONS

McGeoch et al. J. Gen. Virol. (1987) 68, 19–38.

Alexander and Elder, "Carbohydrate Dramatically Influences Immune Reactivity of Antisera to Viral Glycoprotein Antigens," *Science*, 226 (4680): 1328–1330 (Dec. 14, 1984).

Ashley et al., "Comparison of Western Blot (Immunoblot) and Glycoprotein G–Specific Immunodot Enzyme Assay for Detecting Antibodies to Herpes Simplex Virus Types 1 and 2 in Human Sera," *J. Clin. Microbiol.*, 26 (4): 662–667 (Apr. 1988).

Balachandran and Hutt–Fletcher, "Synthesis and Processing of Glycoprotein gG of Herpes Simplex Virus Type 2," *J. Virol.*, 44: 344–355 (1982).

Berman et al., "Detection of Antibodies to Herpes Simplex Virus with a Continuous Cell Line Expressing Cloned Glycoprotein D," *Science*, 222: 524–527 (Nov. 4, 1983).

Caust et al., "Glycosylation, an important modifier of rotavirus antigenicity," *Arch. Virol.*, 96 (3–4): 123–124 (1987).

Corey et al., "Genital Herpes Simplex Virus Infections: Clinical Manifestations, Course, and Complications," *Ann. Int. Med.*, 98: 958–972 (1983).

Douglas, "DNA Viruses: Herpetoviridae", pp. 944–951 in *Principles and Practice of Infectious Diseases* (2d ed.) (Mandrell et al. eds) (1985).

Glorioso et al., "Inhibition of Glycosylation of Herpes Simplex Virus Glycoproteins: Identification of Antigenic and Immunogenic Partially Glycosylated Glycopeptides on the Cell Surface Membrane," *Virol.* 126 (1): 1–18 (Apr. 15, 1983).

Hongo et al., "Effects of glycosylation on the conformation and antigenicity of influenza C viral glycoproteins," *Vaccine*, 3 (3 suppl.): 223–226 (Sep. 1985).

Lee et al., "Detection of Herpes Simplex Virus Type 2–Specific Antibody with Glycoprotein G," *J. Clin. Microbiol.*, 22 (4): 641–644 (Oct. 1985).

Marsden et al., "Characterization of the 92,000–Dalton Glycoprotein Induced by Herpes Simplex Virus Type 2," *J. Virol.*, 50 (2): 547–554 (May 1984).

McGeoch et al., "DNA Sequence and Genetic Content of the HindIII 1 Region in the Short Unique Component of the Herpes Simplex Virus Type 2 Genome: Identification of the Gene Encoding Glycoprotein G, and Evolutionary Comparisons," *J. Gen. Virol.*, 68: 19–38 (1987).

(List continued on next page.)

*Primary Examiner*—Marian C. Knode
*Assistant Examiner*—Jay Williams
*Attorney, Agent, or Firm*—Roberta L. Robins; Barbara G. McClung; Robert P. Blackburn

[57] ABSTRACT

Disclosed are recombinant, synthetically and otherwise biologically produced novel proteins and polypeptides which are encoded by the DNA sequence for HSV-2 glycoprotein G (gG) or fragments of said gG sequence, particularly by the unique sequence for gG or portions of said unique sequence. The unique sequence proteins and polypeptides are serologically active, can be produced easily and safely at low cost, are useful as diagnostic reagents for HSV-2 and as vaccines against HSV-2. Further disclosed are serological assays based on such unique sequence gG proteins and polypeptides that diagnose the presence of herpes simplex virus type 2 (HSV-2) specific antibodies and can differentiate between HSV-2 and herpes simplex virus type 1 (HSV-1) specific antibodies. Such assays are useful to diagnose genital infections, to detect for exposure to HSV-2 and to screen pregnant women to protect newborns from neonatal HSV-2 infection. Also disclosed are antibodies to such gG proteins and polypeptides which are useful therapeutically, diagnostically and for affinity purification. Further, disclosed are purified and isolated DNA molecules which can be used as probes specific for HSV-2 DNA.

17 Claims, 6 Drawing Sheets

OTHER PUBLICATIONS

Plummer, "A Review of the Identification and Titration of Antibodies to Herpes Simplex Viruses Type 1 and 2 in Human Sera," *Cancer Res.*, 33: 1469–1476 (Jun. 1973).

Roizman et al., "Identification and Preliminary Mapping with Monoclonal Antibodies of a Herpes Simplex Virus 2 Glycoprotein Lacking a Known Type 1 Counterpart," *Virol.*, 133: 242–247 (1984).

Serafini–Cessi et al., "Oligosaccharide Chains of Herpes Simplex Virus Type 2 Glycoprotein gG.2," *Archives Biochem. Biophys.*, 240 (2): 866–876 (Aug. 1, 1985).

Su and Courtney, "Inducible Expression of Herpes Simplex Virus Type 2 Glycoprotein Gene gG–2 in a Mammalian Cell Line," *J. Virol.*, 62 (10): 3668–3674 (Oct. 1988).

Sugawara et al., "Operational and Topological Analyses of Antigenic Sites on Influenza C Virus Glycoprotein and Their Dependance on Glycosylation," *J. Gen. Virol.*, 69: 537–547 (1988).

Sullender et al., "Type–Specific Antibodies to Herpes Simplex Virus Type 2 (HSV–2) Glycoprotein G in Pregnant Women, Infants Exposed to Maternal HSV–2 Infection at Delivery, and Infants with Neonatal Herpes," *J. Infect. Diseases,* 157(1): 164–171 (Jan. 1988).

Watson et al., "Herpes Simplex Virus Type–1 Glycoprotein D Gene: Nucleotide Sequence and Expression in *Escherichia coli,"Science,* 218: 381–384 (Oct. 22, 1982).

Weis et al., "An immunologically active chimaeric protein containing herpes simplex virus type 1 glycoprotein D," *Nature,* 302: 72–74 (Mar. 1983).

Whittaker, "Herpelisa II Test Kit (192 Tests), An Enzyme–Linked Immunosorbent Assay for Herpesvirus IgG (Type 1 and 2) Antibody in Human Serum," Whittaker *Bioproducts* Brochure P3134 (May 1988).

Wilcox et al., "The Contribution of Cysteine Residues to Antigenicity and Extent of Processing of Herpes Simplex Virus Type 1 Glycoprotein D," *J. Virol.*, 62 (8): 1941–1947 (Jun. 1988).

| | | | | | |
|---|---|---|---|---|---|
| 1 | CAACAGCGAT | GTTGTTTTCC | CGGGAGGTTC | CCCCGTGGCT | CAATATTGTT |
| 51 | ATGCCTATCC | CCGGTTGGAC | GATCCCGGGC | CCTTGGGTTC | CGCGGACGCC |
| 101 | GGGCGGCAAG | ACCTGCCCCG | GCGCGTCGTC | CGTCACGAGC | CCCTGGGCCG |
| 151 | CTCGTTCCTC | ACGGGGGGGC | TGGTTTTGCT | GGCGCCGCCG | GTACGCGGAT |
| 201 | TTGGCGCACC | CAACGCAACG | TATGCGGCCC | GTGTGACGTA | CTACCGGCTC |
| 251 | ACCCGCGCCT | GCCGTCAGCC | CATCCTCCTT | CGGCAGTATG | GAGGGTGTCG |
| 301 | CGGCGGCGAG | CCGCCGTCCC | CAAAGACGTG | CGGGTCGTAC | ACGTACACGT |
| 351 | ACCAGGGCGG | CGGGCCTCCG | ACCCGGTACG | CTCTCGTAAA | TGCTTCCCTG |
| 401 | CTGGTGCCGA | TCTGGGACCG | CGCCGCGGAG | ACATTCGAGT | ACCAGATCGA |
| 451 | ACTCGGCGGC | GAGCTGCACG | TGGGTCTGTT | GTGGGTAGAG | GTGGGCGGGG |
| 501 | AGGGCCCCGG | CCCCACCGCC | CCCCCACAGG | CGGCGCGTGC | GGAGGGCGGC |
| 551 | CCGTGCGTCC | CCCCGGTCCC | CGCGGGCCGC | CCGTGGCGCT | CGGTGCCCCC |
| 601 | GGTATGGTAT | TCCGCCCCCA | ACCCCGGGTT | TCGTGGCCTG | CGTTTCCGGG |
| 651 | AGCGCTGTCT | GCCCCCACAG | ACGCCCGCCG | CCCCCAGCGA | CCTACCACGC |
| 701 | GTCGCTTTTG | CTCCCCAGAG | CCTGCTGGTG | GGGATTACGG | GCCGCACGTT |
| 751 | TATTCGGATG | GCACGACCCA | CGGAAGACGT | CGGGGTCCTG | CCGCCCCATT |
| 801 | GGGCCCCCGG | GGCCCTAGAT | GACGGTCCGT | ACGCCCCCTT | CCCACCCCGC |
| 851 | CCGCGGTTTC | GACGCGCCCT | GCGGACAGAC | CCCGAGGGGG | TCGACCCCGA |
| 901 | CGTTCGGGCC | CCCCGAACCG | GGCGGCGCCT | CATGGCCTTG | ACCGAGGACA |
| 951 | CGTCCTCCGA | TTCGCCTACG | TCCGCTCCGG | AGAAGACGCC | CCTCCCTGTG |
| 1001 | TCGGCCACCG | CCATGGCACC | CTCAGTCGAC | CCAAGCGCGG | AACCGACCGC |
| 1051 | CCCCGCAACC | ACTACTCCCC | CCGACGAGAT | GGCCACACAA | GCCGCAACGG |

FIG. 1A

1101 TCGCCGTTAC GCCGGAGGAA ACGGCAGTCG CCTCCCCGCC CGCGACTGCA

1151 TCCGTGGAGT CGTCGCCACT CCCCGCCGCG GCGGCGGCAA CGCCCGGGGC

1201 CGGGCACACG AACACCAGCA GCGCCTCCGC AGCGAAAACG CCCCCCACCA

1251 CACCAGCCCC CACGACCCCC CCGCCCACGT CTACCCACGC GACCCCCCGC

1301 CCCACGACTC CGGGGCCCCA AACAACCCCT CCCGGACCCG CAACCCCGGG

1351 TCCGGTGGGC GCCTCCGCCG CGCCCACGGC CGATTCCCCC CTCACCGCCT

1401 CGCCCCCCGC TACCGCGCCG GGGCCCTCGG CCGCCAACGT TTCGGTCGCC

1451 GCGACCACCG C

FIG. 1B

1 NSDVVFPGGS PVAQYCYAYP RLDDPGPLGS ADAGRQDLPR RVVRHEPLGR

51 SFLTGGLVLL APPVRGFGAP NATYAARVTY YRLTRACRQP ILLRQYGGCR

101 GGEPPSPKTC GSYTYTYQGG GPPTRYALVN ASLLVPIWDR AAETFEYQIE

151 LGGELHVGLL WVEVGGEGPG PTAPPQAARA EGGPCVPPVP AGRPWRSVPP

201 VWYSAPNPGF RGLRFRERCL PPQTPAAPSD LPRVAFAPQS LLVGITGRTF

251 IRMARPTEDV GVLPPHWAPG ALDDGPYAPF PPRPRFRRAL RTDPEGVDPD

301 VRAPRTGRRL MALTEDTSSD SPTSAPEKTP LPVSATAMAP SVDPSAEPTA

351 PATTTPPDEM ATQAATVAVT PEETAVASPP ATASVESSPL PAAAAATPGA

401 GHTNTSSASA AKTPPTTPAP TTPPPTSTHA TPRPTTPGPQ TTPPGPATPG

451 PVGASAAPTA DSPLTASPPA TAPGPSAANV SVAATT

FIG. 2

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
( A ) LENGTH: 1461 base pairs
( B ) TYPE: nucleic acid
( C ) STRANDEDNESS: double
( D ) TOPOLOGY: circular ( i i ) MOLECULE TYPE: DNA (genomic)

( x i ) SEQUENCE DESCRIPTION: SEQ ID NO: 1:

```
CAACAGCGAT GTTGTTTTCC CGGGAGGTTC CCCCGTGGCT CAATATTGTT ATGCCTATCC     60
CCGGTTGGAC GATCCCGGGC CCTTGGGTTC CGCGGACGCC GGGCGGCAAG ACCTGCCCCG    120
GCGCGTCGTC CGTCACGAGC CCCTGGGCCG CTCGTTCCTC ACGGGGGGGC TGGTTTTGCT    180
GGCGCCGCCG GTACGCGGAT TTGGCGCACC CAACGCAACG TATGCGGCCC GTGTGACGTA    240
CTACCGGCTC ACCCGCGCCT GCCGTCAGCC CATCCTCCTT CGGCAGTATG GAGGGTGTCG    300
CGGCGGCGAG CCGCCGTCCC CAAAGACGTG CGGGTCGTAC ACGTACACGT ACCAGGGCGG    360
CGGGCCTCCG ACCCGGTACG CTCTCGTAAA TGCTTCCCTG CTGGTGCCGA TCTGGGACCG    420
CGCCGCGGAG ACATTCGAGT ACCAGATCGA ACTCGGCGGC GAGCTGCACG TGGGTCTGTT    480
GTGGGTAGAG GTGGGCGGGG AGGGCCCCGG CCCCACCGCC CCCCCACAGG CGGCGCGTGC    540
GGAGGGCGGC CCGTGCGTCC CCCCGGTCCC CGCGGGCCGC CCGTGGCGCT CGGTGCCCCC    600
GGTATGGTAT TCCGCCCCCA ACCCCGGGTT TCGTGGCCTG CGTTTCCGGG AGCGCTGTCT    660
GCCCCCACAG ACGCCCGCCG CCCCCAGCGA CCTACCACGC GTCGCTTTTG CTCCCCAGAG    720
CCTGCTGGTG GGGATTACGG GCCGCACGTT TATTCGGATG GCACGACCCA CGGAAGACGT    780
CGGGGTCCTG CCGCCCCATT GGGCCCCCGG GGCCCTAGAT GACGGTCCGT ACGCCCCCTT    840
CCCACCCCGC CCGCGGTTTC GACGCGCCCT GCGGACAGAC CCCGAGGGGG TCGACCCCGA    900
CGTTCGGGCC CCCCGAACCG GGCGGCGCCT CATGGCCTTG ACCGAGGACA CGTCCTCCGA    960
TTCGCCTACG TCCGCTCCGG AGAAGACGCC CCTCCCTGTG TCGGCCACCG CCATGGCACC   1020
CTCAGTCGAC CCAAGCGCGG AACCGACCGC CCCCGCAACC ACTACTCCCC CCGACGAGAT   1080
GGCCACACAA GCCGCAACGG TCGCCGTTAC GCCGGAGGAA ACGGCAGTCG CCTCCCCGCC   1140
CGCGACTGCA TCCGTGGAGT CGTCGCCACT CCCCGCCGCG GCGGCGGCAA CGCCCGGGGC   1200
CGGGCACACG AACACCAGCA GCGCCTCCGC AGCGAAAACG CCCCCCACCA CACCAGCCCC   1260
CACGACCCCC CCGCCCACGT CTACCCACGC GACCCCCCGC CCCACGACTC CGGGGCCCCA   1320
AACAACCCCT CCCGGACCCG CAACCCCGGG TCCGGTGGGC GCCTCCGCCG CGCCCACGGC   1380
```

-continued

```
CGATTCCCCC CTCACCGCCT CGCCCCCCGC TACCGCGCCG GGGCCCTCGG CCGCCAACGT    1440

TTCGGTCGCC GCGACCACCG C                                              1461
```

( 2 ) INFORMATION FOR SEQ ID NO: 2:

( i ) SEQUENCE CHARACTERISTICS:
( A ) LENGTH: 486 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO: 2:

```
Asn Ser Asp Val Val Phe Pro Gly Gly Ser Pro Val Ala Gln Tyr Cys
1               5                   10                  15

Tyr Ala Tyr Pro Arg Leu Asp Asp Pro Gly Pro Leu Gly Ser Ala Asp
            20                  25                  30

Ala Gly Arg Gln Asp Leu Pro Arg Arg Val Val Arg His Glu Pro Leu
        35                  40                  45

Gly Arg Ser Phe Leu Thr Gly Gly Leu Val Leu Leu Ala Pro Pro Val
    50                  55                  60

Arg Gly Phe Gly Ala Pro Asn Ala Thr Tyr Ala Ala Arg Val Thr Tyr
65                  70                  75                  80

Tyr Arg Leu Thr Arg Ala Cys Arg Gln Pro Ile Leu Leu Arg Gln Tyr
                85                  90                  95

Gly Gly Cys Arg Gly Gly Glu Pro Pro Ser Pro Lys Thr Cys Gly Ser
            100                 105                 110

Tyr Thr Tyr Thr Tyr Gln Gly Gly Gly Pro Pro Thr Arg Tyr Ala Leu
        115                 120                 125

Val Asn Ala Ser Leu Leu Val Pro Ile Trp Asp Arg Ala Ala Glu Thr
    130                 135                 140

Phe Glu Tyr Gln Ile Glu Leu Gly Gly Glu Leu His Val Gly Leu Leu
145                 150                 155                 160

Trp Val Glu Val Gly Gly Glu Gly Pro Gly Pro Thr Ala Pro Pro Gln
                165                 170                 175

Ala Ala Arg Ala Glu Gly Gly Pro Cys Val Pro Pro Val Pro Ala Gly
            180                 185                 190

Arg Pro Trp Arg Ser Val Pro Pro Val Trp Tyr Ser Ala Pro Asn Pro
        195                 200                 205

Gly Phe Arg Gly Leu Arg Phe Arg Glu Arg Cys Leu Pro Pro Gln Thr
    210                 215                 220

Pro Ala Ala Pro Ser Asp Leu Pro Arg Val Ala Phe Ala Pro Gln Ser
225                 230                 235                 240

Leu Leu Val Gly Ile Thr Gly Arg Thr Phe Ile Arg Met Ala Arg Pro
                245                 250                 255

Thr Glu Asp Val Gly Val Leu Pro Pro His Trp Ala Pro Gly Ala Leu
            260                 265                 270

Asp Asp Gly Pro Tyr Ala Pro Phe Pro Pro Arg Pro Arg Phe Arg Arg
        275                 280                 285

Ala Leu Arg Thr Asp Pro Glu Gly Val Asp Pro Asp Val Arg Ala Pro
    290                 295                 300

Arg Thr Gly Arg Arg Leu Met Ala Leu Thr Glu Asp Thr Ser Ser Asp
305                 310                 315                 320

Ser Pro Thr Ser Ala Pro Glu Lys Thr Pro Leu Pro Val Ser Ala Thr
                325                 330                 335
```

-continued

| | | | | | | | | | | | | | | | |
|---|---|---|---|---|---|---|---|---|---|---|---|---|---|---|---|
| Ala | Met | Ala | Pro | Ser | Val | Asp | Pro | Ser | Ala | Glu | Pro | Thr | Ala | Pro | Ala |
| | | | 340 | | | | | 345 | | | | | 350 | | |
| Thr | Thr | Thr | Pro | Pro | Asp | Glu | Met | Ala | Thr | Gln | Ala | Ala | Thr | Val | Ala |
| | | 355 | | | | | 360 | | | | | 365 | | | |
| Val | Thr | Pro | Glu | Glu | Thr | Ala | Val | Ala | Ser | Pro | Pro | Ala | Thr | Ala | Ser |
| | 370 | | | | | 375 | | | | | 380 | | | | |
| Val | Glu | Ser | Ser | Pro | Leu | Pro | Ala | Ala | Ala | Ala | Ala | Thr | Pro | Gly | Ala |
| 385 | | | | | 390 | | | | | 395 | | | | | 400 |
| Gly | His | Thr | Asn | Thr | Ser | Ser | Ala | Ser | Ala | Ala | Lys | Thr | Pro | Pro | Thr |
| | | | | 405 | | | | | 410 | | | | | 415 | |
| Thr | Pro | Ala | Pro | Thr | Thr | Pro | Pro | Pro | Thr | Ser | Thr | His | Ala | Thr | Pro |
| | | | 420 | | | | | 425 | | | | | 430 | | |
| Arg | Pro | Thr | Thr | Pro | Gly | Pro | Gln | Thr | Thr | Pro | Pro | Gly | Pro | Ala | Thr |
| | | 435 | | | | | 440 | | | | | 445 | | | |
| Pro | Gly | Pro | Val | Gly | Ala | Ser | Ala | Ala | Pro | Thr | Ala | Asp | Ser | Pro | Leu |
| | 450 | | | | | 455 | | | | | 460 | | | | |
| Thr | Ala | Ser | Pro | Pro | Ala | Thr | Ala | Pro | Gly | Pro | Ser | Ala | Ala | Asn | Val |
| 465 | | | | | 470 | | | | | 475 | | | | | 480 |
| Ser | Val | Ala | Ala | Thr | Thr | | | | | | | | | | |
| | | | | 485 | | | | | | | | | | | |

( 2 ) INFORMATION FOR SEQ ID NO: 3:

( i ) SEQUENCE CHARACTERISTICS:
( A ) LENGTH: 1342 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO: 3:

ATTGTTATGC CTATCCCCGG TTGGACGATC CCGGGCCCTT GGGTTCCGCG GACGCCGGGC 60

GGCAAGACCT GCCCCGGCGC GTCGTCCGTC ACGAGCCCCT GGGCCGCTCG TTCCTCACGG 120

GGGGGCTGGT TTTGCTGGCG CCGCCGGTAC GCGGATTTGG CGCACCCAAC GCAACGTATG 180

CGGCCCGTGT GACGTACTAC CGGCTCACCC GCGCCTGCCG TCAGCCCATC CTCCTTCGGC 240

AGTATGGAGG GTGTCGCGGC GGCGAGCCGC CGTCCCCAAA GACGTGCGGG TCGTACACGT 300

ACACGTACCA GGGCGGCGGG CCTCCGACCC GGTACGCTCT CGTAAATGCT TCCCTGCTGG 360

TGCCGATCTG GGACCGCGCC GCGGAGACAT TCGAGTACCA GATCGAACTC GGCGGCGAGC 420

TGCACGTGGG TCTGTTGTGG GTAGAGGTGG GCGGGGAGGG CCCCGGCCCC ACCGCCCCCC 480

CACAGGCGGC GCGTGCGGAG GGCGGCCCGT GCGTCCCCCC GGTCCCCGCG GGCCGCCCGT 540

GGCGCTCGGT GCCCCCGGTA TGGTATTCCG CCCCCAACCC CGGGTTTCGT GGCCTGCGTT 600

TCCGGGAGCG CTGTCTGCCC CCACAGACGC CCGCCGCCCC CAGCGACCTA CCACGCGTCG 660

CTTTTGCTCC CCAGAGCCTG CTGGTGGGGA TTACGGGCCG CACGTTTATT CGGATGGCAC 720

GACCCACGGA AGACGTCGGG GTCCTGCCGC CCCATTGGGC CCCCGGGGCC CTAGATGACG 780

GTCCGTACGC CCCCTTCCCA CCCCGCCCGC GGTTTCGACG CGCCCTGCGG ACAGACCCCG 840

AGGGGGTCGA CCCCGACGTT CGGGCCCCCC GAACCGGGCG GCGCCTCATG GCCTTGACCG 900

AGGACACGTC CTCCGATTCG CCTACGTCCG CTCCGGAGAA GACGCCCCTC CCTGTGTCGG 960

CCACCGCCAT GGCACCCTCA GTCGACCCAA GCGCGGAACC GACCGCCCCC GCAACCACTA 1020

CTCCCCCCGA CGAGATGGCC ACACAAGCCG CAACGGTCGC CGTTACGCCG GAGGAAACGG 1080

-continued

| | | | | | | |
|---|---|---|---|---|---|---|
| CAGTCGCCTC | CCCGCCCGCG | ACTGCATCCG | TGGAGTCGTC | GCCACTCCCC | GCCGCGGCGG | 1140 |
| CGGCAACGCC | CGGGGCCGGG | CACACGAACA | CCAGCAGCGC | CTCCGCAGCG | AAAACGCCCC | 1200 |
| CCACCACACC | AGCCCCCACG | ACCCCCCCGC | CCACGTCTAC | CCACGCGACC | CCCCGCCCCA | 1260 |
| CGACTCCGGG | GCCCCAAACA | ACCCCTCCCG | GACCCGCAAC | CCCGGGTCCG | GTGGGCGCCT | 1320 |
| CCGCCGCGCC | CACGGCCGAT | TC | | | | 1342 |

( 2 ) INFORMATION FOR SEQ ID NO: 4:

( i ) SEQUENCE CHARACTERISTICS:
( A ) LENGTH: 447 amino acids
( B ) TYPE: amino acid
( D ) TOPOLOGY: linear ( i i ) MOLECULE TYPE: protein ( x i ) SEQUENCE DESCRIPTION: SEQ ID NO: 4:

Cys Tyr Ala Tyr Pro Arg Leu Asp Asp Pro Gly Pro Leu Gly Ser Ala
1 5 10 15

Asp Ala Gly Arg Gln Asp Leu Pro Arg Arg Val Val Arg His Glu Pro
20 25 30

Leu Gly Arg Ser Phe Leu Thr Gly Gly Leu Val Leu Leu Ala Pro Pro
35 40 45

Val Arg Gly Phe Gly Ala Pro Asn Ala Thr Tyr Ala Ala Arg Val Thr
50 55 60

Tyr Tyr Arg Leu Thr Arg Ala Cys Arg Gln Pro Ile Leu Leu Arg Gln
65 70 75 80

Tyr Gly Gly Cys Arg Gly Gly Glu Pro Pro Ser Pro Lys Thr Cys Gly
85 90 95

Ser Tyr Thr Tyr Thr Tyr Gln Gly Gly Gly Pro Pro Thr Arg Tyr Ala
100 105 110

Leu Val Asn Ala Ser Leu Leu Val Pro Ile Trp Asp Arg Ala Ala Glu
115 120 125

Thr Phe Glu Tyr Gln Ile Glu Leu Gly Gly Glu Leu His Val Gly Leu
130 135 140

Leu Trp Val Glu Val Gly Gly Glu Gly Pro Gly Pro Thr Ala Pro Pro
145 150 155 160

Gln Ala Ala Arg Ala Glu Gly Gly Pro Cys Val Pro Pro Val Pro Ala
165 170 175

Gly Arg Pro Trp Arg Ser Val Pro Pro Val Trp Tyr Ser Ala Pro Asn
180 185 190

Pro Gly Phe Arg Gly Leu Arg Phe Arg Glu Arg Cys Leu Pro Pro Gln
195 200 205

Thr Pro Ala Ala Pro Ser Asp Leu Pro Arg Val Ala Phe Ala Pro Gln
210 215 220

Ser Leu Leu Val Gly Ile Thr Gly Arg Thr Phe Ile Arg Met Ala Arg
225 230 235 240

Pro Thr Glu Asp Val Gly Val Leu Pro Pro His Trp Ala Pro Gly Ala
245 250 255

Leu Asp Asp Gly Pro Tyr Ala Pro Phe Pro Pro Arg Pro Arg Phe Arg
260 265 270

Arg Ala Leu Arg Thr Asp Pro Glu Gly Val Asp Pro Asp Val Arg Ala
275 280 285

Pro Arg Thr Gly Arg Arg Leu Met Ala Leu Thr Glu Asp Thr Ser Ser
290 295 300

Asp Ser Pro Thr Ser Ala Pro Glu Lys Thr Pro Leu Pro Val Ser Ala

-continued

| | | | | | | | | | | | | | | | |
|---|---|---|---|---|---|---|---|---|---|---|---|---|---|---|---|
| 305 | | | | | 310 | | | | | 315 | | | | | 320 |
| Thr | Ala | Met | Ala | Pro 325 | Ser | Val | Asp | Pro | Ser 330 | Ala | Glu | Pro | Thr | Ala 335 | Pro |
| Ala | Thr | Thr | Thr 340 | Pro | Pro | Asp | Glu | Met 345 | Ala | Thr | Gln | Ala | Ala 350 | Thr | Val |
| Ala | Val | Thr 355 | Pro | Glu | Glu | Thr | Ala 360 | Val | Ala | Ser | Pro | Pro 365 | Ala | Thr | Ala |
| Ser | Val 370 | Glu | Ser | Ser | Pro | Leu 375 | Pro | Ala | Ala | Ala | Ala 380 | Ala | Thr | Pro | Gly |
| Ala 385 | Gly | His | Thr | Asn | Thr 390 | Ser | Ser | Ala | Ser | Ala 395 | Ala | Lys | Thr | Pro | Pro 400 |
| Thr | Thr | Pro | Ala | Pro 405 | Thr | Thr | Pro | Pro | Pro 410 | Thr | Ser | Thr | His | Ala 415 | Thr |
| Pro | Arg | Pro | Thr 420 | Thr | Pro | Gly | Pro | Gln 425 | Thr | Thr | Pro | Pro | Gly 430 | Pro | Ala |
| Thr | Pro | Gly 435 | Pro | Val | Gly | Ala | Ser 440 | Ala | Ala | Pro | Thr | Ala 445 | Asp | Ser | |

( 2 ) INFORMATION FOR SEQ ID NO: 5:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 5:

GGCCGATTCG 10

( 2 ) INFORMATION FOR SEQ ID NO: 6:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 6:

CTAAGCTTAA 10

( 2 ) INFORMATION FOR SEQ ID NO: 7:

( i ) SEQUENCE CHARACTERISTICS:
( A ) LENGTH: 84 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO: 7:

GATCCAGGAA ATACTTACAT ATGAAAGCTA TCTTCGTTCT GAAAGGTTCT CTGGACCGTG 60

ACCCGGAATT CACCATGGAT CCCC 84

( 2 ) INFORMATION FOR SEQ ID NO: 8:

( i ) SEQUENCE CHARACTERISTICS:
( A ) LENGTH: 26 amino acids
( B ) TYPE: amino acid
( D ) TOPOLOGY: linear ( i i ) MOLECULE TYPE: peptide ( x i ) SEQUENCE DESCRIPTION: SEQ ID NO: 8:

His Glu Pro Leu Gly Arg Ser Phe Leu Thr Gly Gly Leu Val Leu Leu
1 5 10 15

Ala Pro Pro Val Arg Gly Phe Gly Ala Pro
20 25

( 2 ) INFORMATION FOR SEQ ID NO: 9:

( i ) SEQUENCE CHARACTERISTICS:
( A ) LENGTH: 26 amino acids
( B ) TYPE: amino acid
( D ) TOPOLOGY: linear ( i i ) MOLECULE TYPE: peptide ( x i ) SEQUENCE DESCRIPTION: SEQ ID NO: 9:

Gln Tyr Gly Gly Cys Arg Gly Gly Glu Pro Pro Ser Pro Lys Thr Cys
1 5 10 15

Gly Ser Tyr Thr Tyr Thr Tyr Gln Gly Gly
20 25

( 2 ) INFORMATION FOR SEQ ID NO: 10:

( i ) SEQUENCE CHARACTERISTICS:
( A ) LENGTH: 66 amino acids
( B ) TYPE: amino acid
( D ) TOPOLOGY: linear ( i i ) MOLECULE TYPE: peptide ( x i ) SEQUENCE DESCRIPTION: SEQ ID NO: 10:

Gly Gly Glu Gly Pro Gly Pro Thr Ala Pro Pro Gln Ala Ala Arg Ala
1 5 10 15

Glu Gly Gly Pro Cys Val Pro Pro Val Pro Ala Gly Arg Pro Trp Arg
20 25 30

Ser Val Pro Pro Val Trp Tyr Ser Ala Pro Asn Pro Gly Phe Arg Gly
35 40 45

Leu Arg Phe Arg Glu Arg Cys Leu Pro Pro Gln Thr Pro Ala Ala Pro
50 55 60

Ser Asp
65

( 2 ) INFORMATION FOR SEQ ID NO: 11:

( i ) SEQUENCE CHARACTERISTICS:
( A ) LENGTH: 26 amino acids
( B ) TYPE: amino acid
( D ) TOPOLOGY: linear ( i i ) MOLECULE TYPE: peptide ( x i ) SEQUENCE DESCRIPTION: SEQ ID NO: 11:

Arg Thr Gly Arg Arg Leu Met Ala Leu Thr Glu Asp Thr Ser Ser Asp
1 5 10 15

Ser Pro Thr Ser Ala Pro Glu Lys Thr Pro
20 25

( 2 ) INFORMATION FOR SEQ ID NO: 12:

( i ) SEQUENCE CHARACTERISTICS:
( A ) LENGTH: 26 amino acids
( B ) TYPE: amino acid -continued ( D ) TOPOLOGY: linear ( i i ) MOLECULE TYPE: peptide ( x i ) SEQUENCE DESCRIPTION: SEQ ID NO: 12:

```
Pro Thr Ser Thr His Ala Thr Pro Arg Pro Thr Thr Pro Gly Pro Gln
1               5                   10                  15

Thr Thr Pro Pro Gly Pro Ala Thr Pro Gly
            20                  25
```

DNA SEQUENCE FOR THE UNIQUE SEQUENCE HERPES SIMPLEX VIRUS TYPE 2-GLYCOPROTEIN G PROTEIN AND METHOD OF EXPRESSING SAID UNIQUE SEQUENCE OF HSV-2GG

RELATED APPLICATIONS

This application is a continuation of U.S. Ser. No. 08/129,021, filed Sep. 29, 1993now abandoned, which in turn is a continutation of U.S. Ser. No. 07/832,982, filed Feb. 10, 1992, now abandoned, which further is a continuation of U.S. Ser. No. 07/351,740, filed May 12, 1989, now abandoned. This application declares priority under 35 USC Section 120 from those prior filed U.S. applications.

FIELD OF THE INVENTION

This invention is in the fields of biochemical engineering and immunochemistry. More particularly, this invention relates to recombinant DNA molecules expressed in appropriate host organisms as well as novel proteins and polypeptide fragments thereof which may be produced recombinantly, synthetically or by other means, such as by, the fragmentation of biologically produced proteins and polypeptides. The recombinant DNA molecules of this invention are characterized by the DNA which codes for proteins and polypeptides from the herpes simplex virus type 2 (HSV-2) glycoprotein G (gG). More specifically, said DNA is that from the unique sequence of glycoprotein G (gG) of HSV-2 or portions of said unique sequence which code for serologically active novel proteins and polypeptides. Said DNA can be used as probes specific for HSV-2 DNA, and said serologically active proteins and polypeptides are useful as reagents for the immunological detection of HSV-2, enabling a diagnostician to differentiate between HSV-2 type-specific antibodies and herpes simplex type 1 (HSV-1) type-specific antibodies. The expressed or synthetically or biologically produced proteins and polypeptides of this invention are further useful for the production of antibodies and as vaccines for HSV-2.

BACKGROUND OF THE INVENTION

The herpes viruses include the herpes simplex viruses, comprising two related variants designated types 1 (HSV-1) and 2 (HSV-Z). Many of the counterpart gene products of HSV-1 and HSV-2 have similar molecular weights and common antigenic determinants. However, clinical manifestations of HSV-1 and HSV-2 differ significantly. Nongenital herpes infections such as common cold sores are primarily caused by HSV-1. Genital and neonatal infections are most usually associated with HSV-2. About 90% of primary genital HSV infections and about 99% of recurrent genital HSV infections are caused by HSV-2. [Sullender et al., *J. Infect. Dis.* 157(1):164–171 (Jan. 1988).]

As estimated by physician consultations, the incidence of symptomatic genital herpes is steadily increasing in the United States, developing among hundreds of thousands of Americans every year. [Sullender et al., *J. Infect. Dis.* 157(1): 164–167 (Jan. 1988); Tapley et al. (eds.), *The Columbia University College of Physicians and Surgeons Complete Home Medical Guide* (1985).] The prevalence of asymptomatic HSV-2 infections has been difficult to determine because of the strong cross-neutralization between HSV-1 and HSV-2 and because of the high incidence of antibody to HSV-1 in the population. [Plummer, *Cancer Res.*, 33: 1469–1476 (June 1973).] As Lee et al. [*J. Clin. Microbiol.*, 22(4): 641–644 at 643 (1985)] point out: "[A] serological assay that can detect HSV-2 antibodies would be of particular epidemiological assistance. However, because of the existence of many common antigens in HSV-1 and HSV-2, specificity of the assay has been a major problem." [Emphasis added; citation omitted.] Specificity of such an assay is important because of the implications of HSV-2 infections both at the epidemiological level, for example, the relation of genital herpes to cervical cancer, and at the individual level, for example, false-positive results can lead to great problems such as improper medical management for pregnant women or undue psychological trauma in patients and their consorts. [Lee et al., id. at 643.] The instant invention provides for a specific serological assay to differentiate accurately and definitively between HSV-1 and HSV-2 antibodies.

During the past 20 years, the incidence of neonatal HSV-2 infection has increased significantly, paralleling the increased incidence of genital HSV-2 infection in pregnant females—approximately a nine-fold increase from 1966 to 1979. [Hampar et al., U.S. Pat. No. 4,764,459 (Aug. 16, 1988).] A systemic HSV-2 infection in a newborn can cause serious problems, including blindness, neurological problems, mental retardation and even death. The major source of neonatal HSV-2 infection is via contact with the infected genital tract of the mother at the time of delivery. [Corey et al., *Ann. Int. Med.*, 98:958–972 (1983).] Transmission of HSV-2 from mother to infant can occur during symptomatic or asymptomatic maternal infection. [Corey et al., id.] Studies have indicated that over 70% of infants with neonatal HSV-2 infection had mothers who were asymptomatic at the time of delivery. [Whitley et al., *Pediatrics*, 66:495–501 (1980).] The overall risk of neonatal infection has been estimated to be about 10% in women with primary or recurrent HSV-2 infection after 8 months' gestation and 40% if the HSV-2 virus is present at the time of delivery. [Douglas, "DNA Viruses: Herpetoviridae" in *Principles and Practice of Infectious Diseases* (2d Ed.) (Mandrell et al., eds. (1985).]

The recommended procedure for a pregnant woman suspected of harboring a HSV-2 infection is to perform weekly tissue culture confirmation tests to determine whether HSV-2 is being released into the birth canal. Such procedures are costly and, further, the tissue culture tests are limited by the timing of taking the samples, that is, only at certain points during the infectious cycle are samples containing live virus obtainable; for example, live virus is obtainable during the actively shedding stage in the cycle but not later when the viral vesicles are drying. [See Spruance et al. *Infect. Immun.* 36(3):907–910 (June 1982); and Spruance et al., *N. Engl. J. Med.* 297(2): 69–75 (Jul. 14, 1977).] Therefore, the use of tissue culture tests is limited to the high risk category of pregnant women who show either a) a history of recurrent genital HSV-2 infection, b) active disease during pregnancy, or c) sexual partners with proven HSV-2 infection. If an active infection is apparent, a cesarean delivery, with its associated risks, is performed as a protective measure for the baby. [Hampar et al., supra]. However, as noted above, most infants with neonatal infection due to HSV-2 are born to mothers with no history of genital herpes. Because asymptomatic intrapartum shedding of HSV-2 from the mother's cervical or vulval areas appear to be an important source of neonatal infection, a rapid, reliable and inexpensive serological screening test to identify pregnant women potentially harboring HSV-2 is needed. [Corey et al., supra]. This invention provides for such a screening test.

The serological assays of this invention are based upon recombinantly, synthetically or biologically produced proteins and polypeptides specific for HSV-2 antibodies. Such proteins and polypeptides are encoded by a unique DNA sequence, or fragments thereof, of the envelope protein, glycoprotein G (gG), of HSV-2, which sequence is not found in HSV-1. McGeoch et al. [*J. Gen. Virol,* 68: 19–38 (1987)] identified the gene coding for gG in HSV-2, delineated its nucleotide and amino acid sequences, and pointed out (at p. 19) that the HSV-2 DNA contains "an extra sequence of about 1460 base pairs" which the HSV-1 gG gene does not have.

Both HSV-2 gG and HSV-1 gG have segments of 153 identical amino acids at their carboxyl-terminal end which contain their putative transmembrane anchor domain (McGeoch et al., id.). However, HSV-2 gG contains an additional segment of 487 unique amino acids which contain the putative type-2 specific epitopes observed with gG, and which are coded for by the extra "about 1460 base pairs" identified by McGeoch et al. Roizman et al., *Virology,* 133: 242–247 (1984) and Marsden et al., *J., Virol.,* 50(2): 547–554 (May 1984) independently discovered HSV-2 gG and developed monoclonal antibodies to it. Roizman et al. described two murine monoclonal antibodies that react with HSV-2 type-specific epitopes of HSV-2 gG and proved that gG was distinct from other HSV-2 envelope glycoproteins, namely, gB, gC and gD.

Use of the HSV-2 gG to detect HSV-2 type-specific antibodies has been reported by Lee et al. [J. Clin. Microbiol., 22(4): 641–644 (Oct. 1985)], Sullender et al. [*J. Inf. Dis.,* 157(1): 164–171 (Jan. 1988)], and Ashley et al. [*J. Clin. Microbiol.,* 26(4): 662–667 (April 1988)]. In each of these studies, immunoaffinity purified, native, full-length, glycosylated gG was employed. Since full-length gG was used, the assays were subject to cross-reactivity with HSV-1 antibodies in the test sera because of the commonality of certain domains in both HSV-1 and HSV-2 gG. Sullender et al. and Ashley et al. suggest the possible clinical use of the HSV-2 gG antibody assay in the diagnosis of genital infections and also in screening pregnant women. However, their assays, requiring the culturing of HSV-2, isolation of the virus and affinity purifying HSV-2 gG from viral lysate antigen preparations with monoclonal antibodies to HSV-2, are expensive to prepare and basically research tools at this time.

Hampar et al. [U.S. Pat. No. 4,764,459 (Aug. 16, 1988)] claims immunoassay methods for detecting antibodies to either HSV-1 or HSV-2 wherein the patients' sera are absorbed with heterologous virus-infected cell extracts to remove intertypic cross-reacting antibodies and then applied to microtiter plates containing the target antigens, either immunoaffinity purified HSV-1 glycoproteins (gC and/or gD) or HSV-2 glycoproteins (gD and/or gF).

Markoulatos et al. [European Patent App. Pub. No. 263, 025 (pub. Apr. 6, 1988)] discloses antigenic glycoprotein fractions of HSV-1 and HSV-2 (gC) and HSV-1 and HSV-2 (gD), purified from respectively infected cells, and claims their use to differentiate between HSV-1 and HSV-2 infections.

Su et al. [*J. Virol.,* 62(10): 3668–3674 (Oct. 1988) report expressing HSV-2 gG in a mammalian cell line. The gG expressed was full length and glycosylated.

Burke et al. [U.S. Pat. No. 4,618,578 (Oct. 21, 1986)] claims methods and compositions for recombinantly producing in yeast polypeptides which are immunologically cross-reactive with glycoprotein D (gD) of HSV-1 and HSV-2. Burke et al. state (at col. 2 lines 6–9) that the "[p]roduction of gD in a yeast host provides the advantages of high levels of expression and modification of the polypeptides not available with prokaryotic hosts . . . "

Watson et al., [*Science,* 218: 381–384 (Oct. 22, 1982)], report the expression of a HSV-1 gycoprotein D (gD) gene in *Escherichia coli* (*E. coli*). Watson et al. state that the fusion of the gD coding region with the *E. coli* lac promoter enabled them to synthesize a gD-related polypeptide, which when injected into rabbits elicited neutralizing antibody to both HSV-1 and HSV-2. Weis et al. [*Nature,* 302: 72–74 (March 1983) report higher level of expression of gD in *E. coli*, wherein a hybrid gene encoding a chimaeric protein containing HSV-1 gD, bacteriophage lambda Cro and *E. coli* beta-galactosidase protein was constructed.

Berman et al., EP 139417 [European Pat. App. Pub. No. 139,417 (pub. Feb. 2 1989)] discloses the expression of HSV-1 glycoprotein D (gD) in Chinese hamster ovary cells (CHO). Claimed therein are vaccines against HSV-1 and HSV-2 comprising at least one glycoprotein of HSV-1 or HSV-2, preferably gD or gC.

Kino et al. [U.S. Pat. No. 4,661,349 (Apr. 28, 1987)] claims a HSV subunit vaccine effective against both HSV-1 and HSV-2 which comprises a highly purified native glycoprotein B (gB) common to both serotypes. Cohen et al. [U.S. Pat. No. 4,762,708 (Aug. 9, 1988)] discloses immunologically active preparations of purified, native HSV envelope glycoproteins, gD-1 and gD-2, useful in vaccines against HSV-1 and HSV-2.

At this time, the only commercially available means of differentially diagnosing a HSV-2 infection from a HSV-1 infection is by a monoclonal antibody-based tissue culture confirmation test which is relatively expensive compared to a blood test and time consuming, taking from at least 24 to 72 hours. Further, such tissue culture confirmation tests are limited because of the above-noted problems associated with obtaining tissue specimens with viable virus. Further, the tissue culture confirmation tests are prohibitively expensive for use in screening asymptomatic carriers of HSV-2. The instant invention provides a substantially cheaper, much quicker and non-time dependent method of serologically identifying HSV-2 type-specific antibodies.

Conventional wisdom in the immunochemistry art appears to consider native glycosylation patterns of antigens important to the conformational aspects of epitopes and necessary for serotype specificity. [See: Berman et al., *Science,* 222: 524–527 at 525 (Nov. 4, 1983); Wilcox et al., *J. Virol.,* 62(6): 1941–1947 (June 1988); Sugawara et al., *J. Gen. Virol.,* 69 (pt. 3): 537–547 (March 1988); Caust et al., *Arch. Virol.,* 96(3–4): 123–124 (1987); Hongo et al., *Vaccine,* 3(3 suppl.):223–226 (Sept. 1985); Alexander et al., *Science,* 226 (4680): 1328–1330 (Dec. 14, 1984); Wayne et al., supra at pp. 1–2; but see: Glorioso et al., *Virol.,* 126(1): 1–18 (Apr. 15, 1983) (wherein it is stated at p. 16: "Although carbohydrate does not appear to be essential for maintenance of antigenicity, it cannot be ruled out that the carbohydrate moieties may play an important role in protein conformation and that some antigenic determinant sites are formed as a consequence of protein secondary structure".] The instant invention controverts such conventional wisdom in that the recombinantly produced proteins and polypeptides of this invention which are type-specific for HSV-2 antibodies can be nonglycosylated, having been expressed in a prokaryotic host.

SUMMARY OF THE INVENTION

This invention is directed to novel proteins and polypeptides encoded by the HSV-2 gG gene or fragments thereof and to the biochemical engineering of the HSV-2 gG gene or fragments thereof into suitable expression vectors; transformation of host organisms with such expression vectors; and production of HSV-2 gG proteins and polypeptides by recombinant, synthetic or other biological means. Such recombinant gG proteins and polypeptides can be glycosylated or nonglycosylated and can be purified to substantial purity according to methods described herein. The invention further concerns such gG polypeptides and proteins which are synthetically or biologically prepared. One use of such gG proteins and polypeptides is as vaccines.

Further this invention concerns recombinant DNA molecules comprising a DNA sequence that encodes not only a HSV-2 gG protein or polypeptide but also an amino acid sequence of a protein/polypeptide which is not immunogenic to humans and which is not typically reactive to antibodies in human bodily fluids. An example of such a DNA sequence is the alpha-peptide coding region of beta-galactosidase. Further, claimed herein are such recombinant fused protein/polypeptides which are substantially pure and non-naturally occurring.

Further, this invention concerns purified and isolated DNA molecules comprising the unique sequence of HSV-2 gG or fragments thereof, including the nucleotide sequence from the unique sequence shown in FIGS. 1A–1B from nucleotide 45 to nucleotide 1386. Said DNA molecules can be used as probes specific for HSV-2 DNA.

More particularly, the invention is directed to biochemical engineering wherein the fragment of the gG gene is from the unique sequence or fragments of the unique sequence and wherein the gG proteins and polypeptides produced are unique sequence gG proteins and polypeptides which similarly can be synthetically or naturally prepared.

A further aspect of this invention relates to the therapeutic and diagnostic use of antibodies to such gG and unique sequence gG proteins and polypeptides, as well as the use of such antibodies for affinity purifying HSV-2 gG proteins and polypeptides.

A still further aspect of this invention relates to serological assays for HSV-2 type-specific antibodies employing the recombinantly, synthetically or otherwise biologically produced unique sequence gG proteins and polypeptides of this invention. This aspect of the invention overcomes the problems of nonspecificity of previously reported serological assays to diagnose HSV-2 infections. Thus the present invention fills the needs referred to above for specific serological assays to differentiate between HSV-1 and HSV-2 type-specific antibodies and for screening tests to detect from the population of asymptomatic individuals, the carriers of HSV-2 type-specific antibodies. Such a screening test is especially important in relation to the population of pregnant women to avert neonatal infections.

Such serological assays can be embodied in test kits comprising a solid phase coated with unique sequence gG proteins and polypeptides. The invention also provides for test kits further comprising antibodies to such unique sequence gG proteins and polypeptides to identify the presence of HSV-2 in human bodily fluids, preferably vital vesicle fluid.

BRIEF DESCRIPTION OF THE FIGURES

FIGS. 1A–1B show the nucleotide sequence for the unique sequence of HSV-2 gG. [SEQ. ID. NO.: 1]

FIG. 2 shows the amino acid sequence which is encoded by the HSV-2 gG unique sequence. [SEQ. ID. NO.: 2]

DETAILED DESCRIPTION

Definitions

Figure 3:
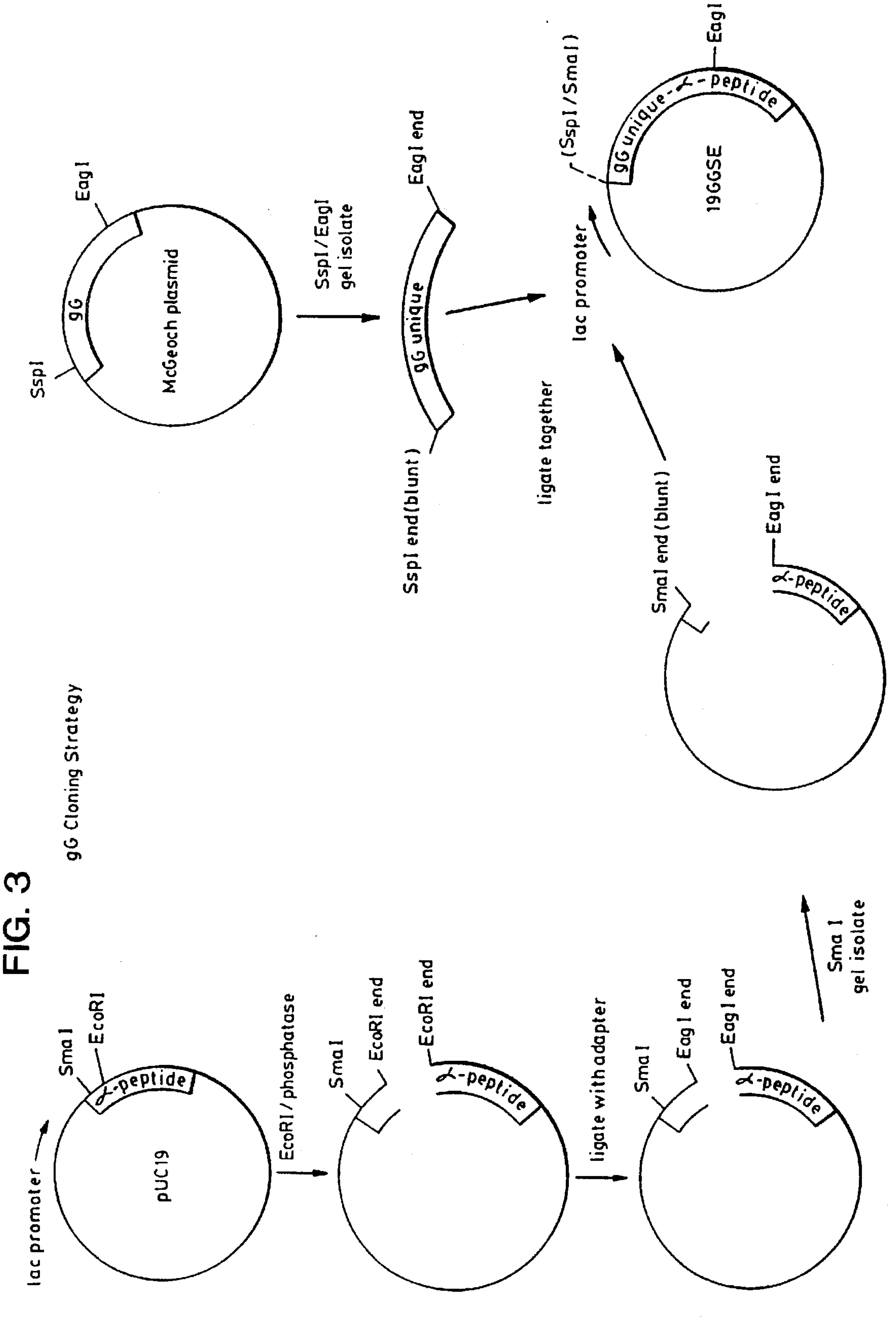
FIG. 3 schematically outlines the construction of plasmid 19gGSE.
Figure 4:
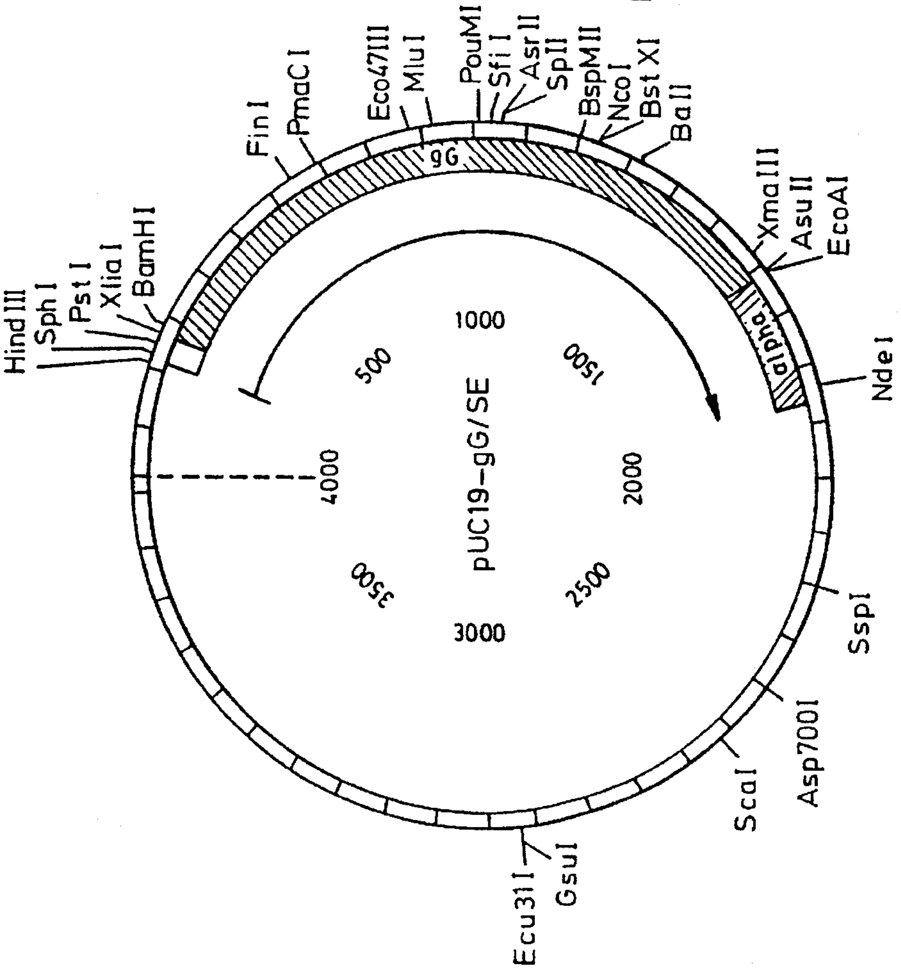
FIG. 4 is a map of plasmid 19gGSE.

The term "HSV-2 gG" refers herein to the envelope protein of HSV-2, glycoprotein G, which is encoded by a 2097 base pair gene as outlined in McGeoch et al., supra.

The phrase "serologically active" is herein defined to mean that the protein or polyeptide modified by that phrase are capable of detecting HSV-2 type-specific antibodies in patient samples, that is, in human bodily fluids, including but not limited to, blood, lymph, mucous, tears, urine, spinal fluid, saliva, but most usually sera. Functionally, serological activity can be established by the immunoblot procedures described herein which are confirmed by tissue culture tests.

The phrase "unique sequence of HSV-2 gG" is herein defined to mean a nucleic acid sequence coding for a portion of the envelope protein glycoprotein G (gG) of HSV-2 which is specific for HSV-2. Said nucleic acid sequence of gG is about 1461 base pairs, coding for a sequence of about 486 amino acids. The nucleotide sense sequence for the unique sequence of HSV-2 gG is shown in FIG. 1, and the amino acid sequence encoded thereby is shown in FIG. 2. McGeoch et al. [supra at p. 19] refers to said unique sequence as "a sequence of about 1460 base pairs in the coding region of gene US4" of HSV-2 which was not found in the HSV-1 US4 gene. The phrase "unique sequence of HSV-2 gG" is herein interpreted to include nucleotide sequences which are substantially the same and have substantially the same biological activity as said unique sequence of HSV-2 gG.

The phrase "gG proteins and polypeptides" is herein defined to mean proteins and polypeptides which are encoded by the HSV-2 glycoprotein G DNA sequence as outlined in McGeoch et al., supra, which article is herein incorporated by reference, or by fragments of said gG DNA sequence. The phrase "gG proteins and polypeptides" is herein interpreted to include proteins and polypeptides which have substantially the same amino acid sequences and which have substantially the same biological activity as the "gG proteins and polypeptides".

The phrase "unique sequence gG proteins and polypeptides" is herein defined to mean proteins and polypeptides which are encoded by the unique sequence of HSV-2 gG or fragments thereof. The phrase "unique sequence gG proteins and polypeptides" is herein interpreted to include proteins and polypeptides which have substantially the same amino acid sequences and which have substantially the same biological activity as the "unique sequence gG proteins and polypeptides".

The phrase "recombinant DNA molecule" is herein defined to mean a hybrid DNA sequence comprising at least two nucleotide sequences, the first sequence not normally being found together in nature with the second.

The phrase "expression control sequence" is herein defined to mean a DNA sequence of nucleotides that controls and regulates expression of structural genes when operatively linked to those genes.

There are twenty main "amino acids", each of which is specified by a different arrangement of three adjacent DNA nucleotides (triplet code or codon), and which are linked together in a specific order to form a characteristic protein. A one-letter convention is used herein to identify said amino acids, as, for example, in FIG. 2, which convention is outlined in Table 1.

TABLE 1

| Amino Acid | One-Letter Symbol |
|---|---|
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

A "polypeptide" is a chain of amino acids covalently bound by peptide linkages and is herein considered to be composed of 50 or less amino acids.

A "protein" is defined herein to be a polypeptide composed of more than 50 amino acids.

A "cloning vehicle" is herein defined to mean a plasmid, phage DNA or other DNA sequences which are able to replicate in a host cell, characterized by one or more endonuclease recognition sites at which such DNA sequences may be cut in a determinable fashion without attendant loss of an essential biological function of the DNA, for example, replication, production of coat proteins or loss of promoter or binding sites, and which preferably contains a marker suitable for use in the identification of transformed cells, for example, tetracycline resistance or an enzyme that effects a color change upon addition of an appropriate substrate. A cloning vehicle is alternately termed a vector.

It is understood that because of the degeneracy of the genetic code, that is, that more than one codon will code for one amino acid [for example the codons TTA, TTG, CTT, CTC, CTA and CTG each code for the amino acid leucine (L)], that variations of the nucleotide sequence of FIG. 1, wherein one codon is substituted for another, would produce a substantially equivalent protein or polypeptide according to this invention. All such variations in the nucleotide sequence of HSV-2 gG are included within the scope of this invention.

It is further understood that the HSV-2 gG DNA unique sequence herein described and shown in FIG. 1 represents only the precise structure of the naturally occurring nucleotide sequence. It is expected that slightly modified nucleotide sequences will be found or can be modified by techniques known in the art to code for similarly serologically active proteins and polypeptides, and such nucleotide sequences and proteins/polypeptides are considered to be equivalents for the purpose of this invention. DNA having equivalent codons is considered within the scope of the invention, as are synthetic DNA sequences that encode proteins/polypeptides homologous or substantially homologous to HSV-2 gG and HSV-2 unique sequence gG proteins/polypeptides and as are DNA sequences that hybridize to the sequences coding for HSV-2 gG and unique sequence gG proteins/polypeptides, as well as those sequences but for the degeneracy of the genetic code would hybridize to said HSV-2 gG and unique gG sequences. Further, DNA sequences which are complementary to the gG sequences referred to herein are within the scope of this invention. Such modifications and variations of DNA sequences as indicated herein are considered to result in sequences that are substantially the same as the HSV-2 gG and unique sequence gG sequences outlined herein. Typically, such related nucleotide sequences are substantially the same which fall into the definition of substantially homologous.

Further, it will be appreciated that the amino acid sequence of HSV-2 gG can be modified by genetic techniques. One or more amino acids can be deleted or substituted. Such amino acid changes, especially if in a region which is not within an epitope of the polypeptide, may not cause any measurable change in the serological activity of the protein or polypeptide. The resulting protein or polypeptide will have substantially the same amino acid sequence and substantially the same serological activity and is within the scope of the invention.

Preparation of HSV-2 gG Proteins and Polypeptides

The HSV-2 gG proteins and polypeptides of this invention, preferably the HSV-2 unique sequence gG proteins and polypeptides, can be prepared in a variety of ways according to this invention. A preferred method to prepare HSV-2 gG proteins is by recombinant means. Representative recombinant methods of this invention are described infra under Cloning of HSV-2 gG or Fragments Thereof, Expression of HSV-2 gG Protein/Polypeptides, and Examples 1–4.

The HSV-2 gG proteins and polypeptides of this invention can further be prepared synthetically or biologically, that is, by cleaving longer proteins and polypeptides enzymatically and/or chemically. Said synthetic and biologic methods are described in detail infra under the heading Synthetic and Biologic Production of HSV-2 gG Protein and Polypeptide Fragments Thereof. Such methods are preferred for preparing HSV-2 gG polypeptides, as those defined under the heading Epitopes infra which delineate preferred serologically active regions of HSV-2 gG.

Cloning of HSV-2 gG or Fragments Thereof

The glycoprotein G of HSV-2 is encoded by a 2097 base pair gene. McGeoch et al. provides the nucleotide sequence for the entire gG gene; McGeoch et al. is herein incorporated by reference. A segment of said gG gene, base pairs 99–1559, is unique to HSV-2 gG, that is, said segment is not found in the HSV-1 gG gene. A portion of the unique sequence of HSV-2 gG, base pairs 143–1484, representing 92% of the unique sequence, was cloned and expressed according to this invention as shown in Example 1, below. The relationship of the aforementioned three nucleotide sequences can be diagrammatically illustrated as follows:

| | |
|---|---|
| HSV-2 gG gene | 1 ------------------------ 2097 |
| Unique gG sequence | 99 ------------------ 1559 |
| Fragment of unique sequence cloned in Ex. 1 | 143 ---------- 1484 |

The unique sequence of gG illustrated as base pairs 99 to 1559 above is shown herein as base pairs 1 to 1461 in FIG.

1 [SEQ. ID. NO.: 1]. The fragment of the unique sequence cloned in Example 1 represents base pairs 45 to 1386 of FIG. 1 [SEQ. ID. NO.: 3]; said cloned sequence codes for the amino acid sequence from amino acid 16 to amino acid 462 [SEQ. ID. NO.: 4] as shown in FIG. 2.

The plasmid 19gGSE, constructed in accordance with Example 1, is only representational of the many possible DNA recombinant molecules that can be prepared in accordance with this invention. Depending on the restriction endonucleases employed, all or part of the gG 2097 base pair sequence or all or part of the 1461 base pair unique sequence may be cloned, expressed and used in accordance with this invention.

An appropriate starting material for isolating the HSV-2 gG gene or portions thereof is the Hind IIII region of HSV-2 strain HG52. McGeoch et al. describe at page 20 inserting said Hind IIII fragment into the Hind III site of pAT153 [commercially available from Amersham; see Bolivar et al., *Gene,* 2:95 (1977) and Twigg and Sherratt *Nature,* 283: 216 (1980)] to construct a plasmid referred to in the Examples below. An alternative source for the HSV-2 gG DNA would be to digest the whole HSV-2 DNA (isolated according to methods well known in the art) with Hind III, and ligate the digested fragments into the Hind III site of the commercially available pAT53. Then an oligonucleotide of about 50 base pairs may be synthesized according to methods well known in the art [for example, with an Applied Biosystems (Foster City, Calif.) DNA synthesizer] that is complementary to an appropriate length of the Hind III fragment of interest, thereby screening the pAT153 clones for a correct clone containing the Hind III fragment.

Useful restriction enzymes according to this invention may include enzymes that cleave DNA in such a way that the DNA fragment generated contains portions of the gG unique sequence. Restriction enzymes employed in the Examples herein include SspI, EagI, EcoRI and SmaI. Other restriction endonucleases may be similarly useful in accordance with this invention. Their selection may be made by those of skill in the art on due consideration of the factors set out herein without departing from the scope of the invention.

A representative cloning vehicle used in Examples 1 and 2, below, is pUC19. Said plasmid is described in Yanisch-Perron et al., *Gene,* 33:103 (1985) and is constructed from source materials available from Bethesda Research Laboratories. However, a wide variety of host-cloning vehicle combinations may be usefully employed in cloning the double-stranded HSV-2 gG DNA isolated as described herein. For example, useful cloning vehicles may include chromosomal, nonchromosomal and synthetic DNA sequences such as various known bacterial plasmids such as pBR322, other *E. coli* plasmids and their derivatives and wider host range plasmids such as RP4, phage DNA such as the numerous derivatives of phage lambda, e.g., NB989 and vectors derived from combinations of plasmids and phage DNAs such as plasmids which have been modified to employ phage DNA expression control sequences.

Useful hosts may be eukaryotic or prokaryotic and include bacterial hosts such as *E. coli* strains CAG456, JM103, N4830, X1776, X2282, HB101 and MRC1 and strains of Pseudomonas, *Bacillus subtilis* and other bacilli, yeasts and other fungi, animal or plant hosts such as animal or plant cells in culture, insect cells and other hosts. Preferred hosts in accordance with this invention are *E. coli* strains, more preferably *E. coli* strains CAG456, JM103 and N4830.

Of course, not all hosts may be equally efficient. The particular selection of host-cloning vehicle combination may be made by those of skill in the art after due consideration of the principles set forth herein without departing from the scope of this invention.

Furthermore, within each specific vector, various sites may be selected for insertion of the isolated double-stranded DNA. These sites are usually designated by the restriction enzyme or endonuclease that cuts them. For example, in pBR322 the PstI site is located in the gene for penicillinase between the nucleotide triplets that code for amino acids 181 and 182 of the penicillinase protein. FIG. 3 displays for illustrative purposes, some of the restriction sites in the McGeoch et al. plasmid and in pUC19.

The particular site chosen for insertion of the selected DNA fragment into the cloning vehicle to form a recombinant DNA molecule is determined by a variety of factors. These include size and structure of the protein or polypeptide to be expressed, susceptibility of the desired protein or polypeptide to endoenzymatic degradation by the host cell components and contamination by its proteins, expression characteristics such as the location of start and stop codons, and other factors recognized by those of skill in the art. Since the expression process is not fully understood, none of these factors alone absolutely controls the choice of insertion site for a particular protein or polypeptide. Rather the site chosen effects a balance of these factors and not all sites may be equally effective for a given protein.

Figure 6A:
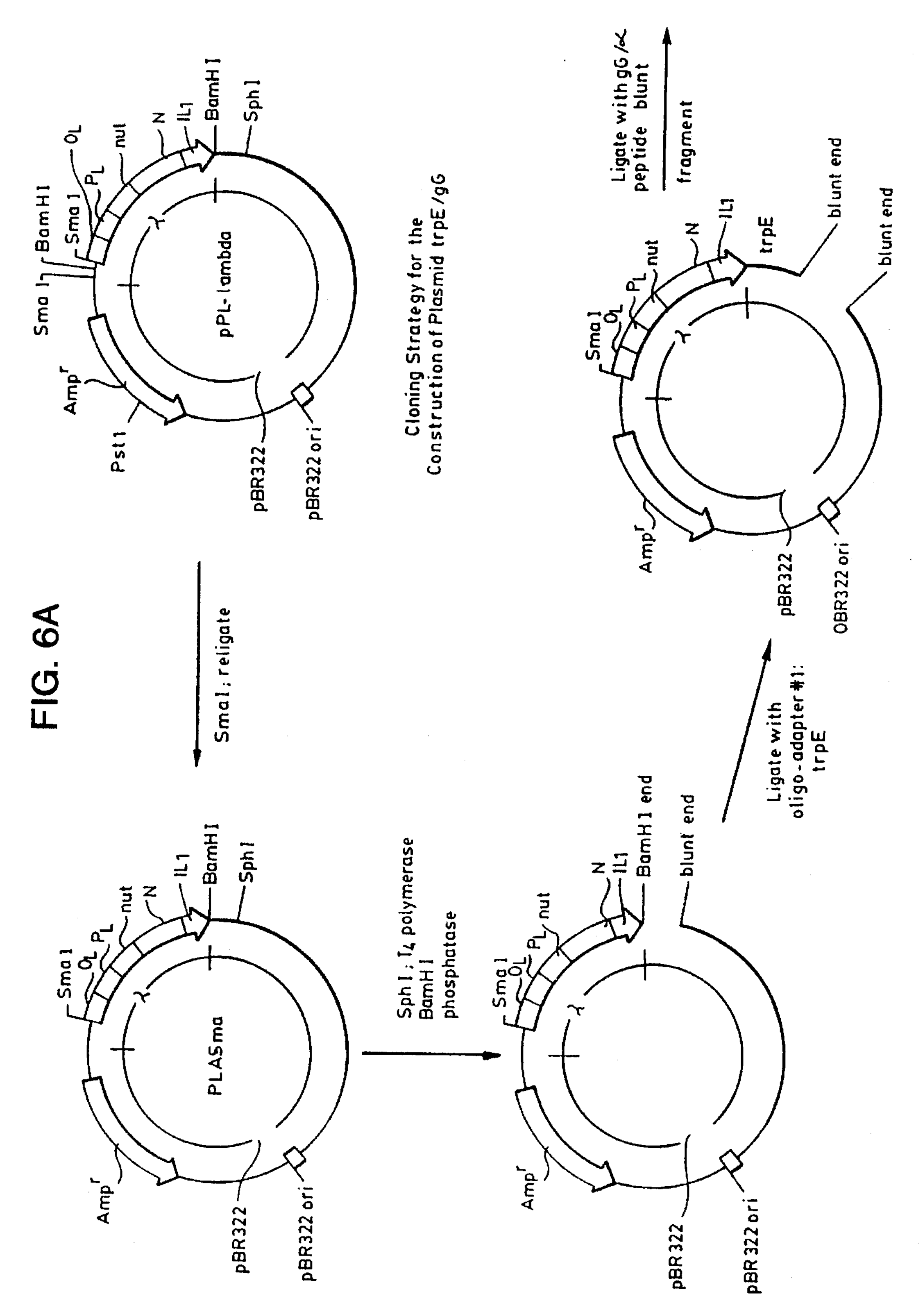
FIGS. 6A–6B schematically outline the construction of plasmid trpE/gG.
Figure 6B:
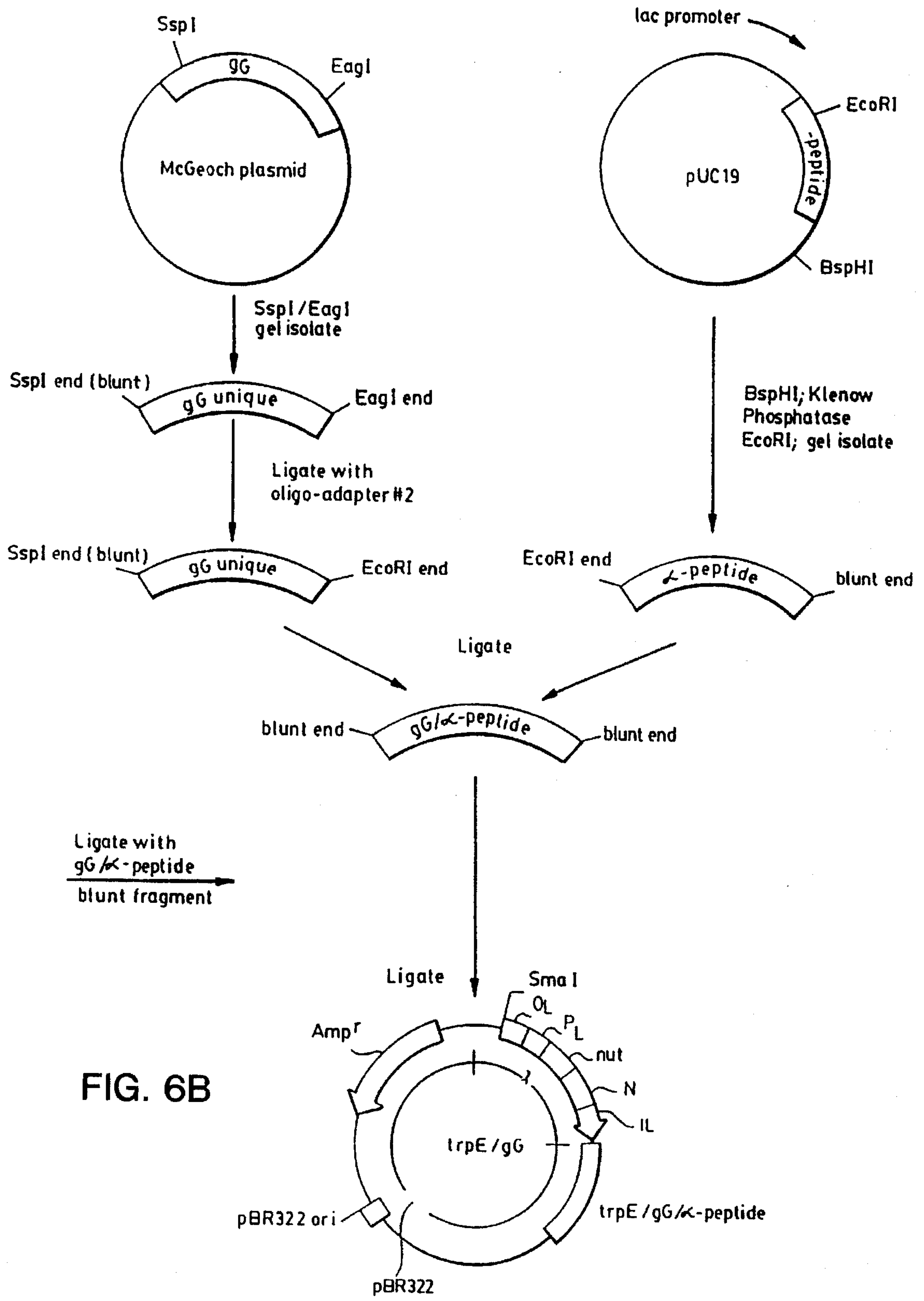

Although several methods are known in the art for inserting foreign DNA into a cloning vehicle to form a recombinant DNA molecule, methods preferred in accordance with this invention are displayed in FIGS. 3 and 6A–B.

Of course, other known methods of inserting DNA sequences into cloning vehicles to form recombinant DNA molecules are equally useful in this invention. These include, for example, direct ligation wherein the same restriction endonuclease is employed to cleave the HSV-2 gG DNA and the cloning vehicle.

It should, of course, be understood that the nucleotide sequence or gene fragment inserted at the selected restriction site of the cloning vehicle may include nucleotides which are not part of the actual structural gene for the desired protein or may include only a fragment of that structural gene. It is only required that whatever DNA sequence is inserted, the transformed host will produce a protein or polypeptide displaying epitopes of HSV-2 gG, more preferably epitopes from the unique sequence gG which recognize type-specific HSV-2 antibodies.

The recombinant DNA molecule containing the hybrid gene may be employed to transform a host so as to permit that host (transformant) to express the structural gene or fragment thereof and to produce the protein or polypeptide for which the hybrid DNA codes. The recombinant DNA molecule may also be employed to transform a host so as to permit that host on replication to produce additional recombinant DNA molecules as a source of HSV-2 gG DNA and fragments thereof. The selection of an appropriate host for either of these uses is controlled by a number of factors recognized by the art. These include, for example, compatibility with the chosen vector, toxicity of the co-products, ease of recovery of the desired protein or polypeptide, expression characteristics, biosafety and costs. Again, since the mechanisms of expression are not fully understood, no absolute choice of host may be made for a particular recombinant DNA molecule or protein or polypeptide from any of these factors alone. Instead, a balance of these factors may be struck with the realization that not all hosts may be equally effective for expression of a particular recombinant DNA molecule.

As indicated above, the recombinant DNA molecule may be used to transform a host so as to permit the host upon replication to produce additional recombinant DNA molecules as a source of HSV-2 gG DNA and fragments thereof. Said DNA molecules can be purified and isolated by methods well known in the art to create DNA probes.

When the DNA sequence for the probe is from the HSV-2 unique sequence or fragments thereof, said probes are specific for HSV-2 DNA.

Expression of HSV-2 gG Proteins/Polypeptides

Where the host cell is a procaryote such as *E. coli*, competent cells which are capable of DNA uptake are prepared from cells harvested after exponential. growth phase and subsequently treated by the $CaCl_2$ method by well known procedures. Transformation can also be performed after forming a protoplast of the host cell.

Where the host used is an eucaryote, transfection method of DNA as calcium phosphate-precipitate, conventional mechanical procedures such as microinjection, insertion of a plasmid encapsulated in red blood cell hosts or in liposomes, treatment of cells with agents such as lysophosphatidyl-choline or use of virus vectors, or the like may be used.

The level of production of a protein or polypeptide is governed by two major factors: the number of copies of its gene or DNA sequence encoding for it within the cell and the efficiency with which these gene and sequence copies are transcribed and translated. Efficiencies of transcription and translation (which together comprise expression) are in turn dependent upon nucleotide sequences, normally situated ahead of the desired coding sequence. These nucleotide sequences or expression control segpences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to known expression control sequences so as to favor higher levels of expression. This having been achieved, the newly engineered DNA fragment may be inserted into a multicopy plasmid or a bacteriophage derivative in order to increase the number of gene or sequence copies within the cell and thereby further improve the yield of expressed protein.

Several expression control sequences may be employed. These include the operator, promoter and ribosome binding and interaction sequences (including sequences such as the Shine-Dalgarno sequences) of the lactose operon of *E. coli* ("the lac system"), the corresponding sequences of the tryptophan synthetase system of *E. coli* ("the trp system"), a fusion of the trp and lac promoter ("the tac system"), the major operator and promoter regions of phage λ ($O_LP_L$ and $O_RP_{R'}$), and the control region of the phage fd coat protein. DNA fragments containing these sequences are excised by cleavage with restriction enzymes from the DNA isolated from transducing phages that carry the lac or trp operons, or from the DNA of phage λ or fd. These fragments are then manipulated in order to obtain a limited population of molecules such that the essential controlling sequences can be joined very close to, or in juxtaposition with, the initiation codon of the coding sequence.

The fusion product is then inserted into a cloning vehicle for transformation of the appropriate hosts and the level of antigen production is measured. Cells giving the most efficient expression may be thus selected. Alternatively, cloning vehicles carrying the lac, trp or λ $P_L$ control system attached to an initiation codon may be employed and fused to a fragment containing a sequence coding for a gG protein or polypeptide such that the gene or sequence is correctly translated from the initiation codon of the cloning vehicle.

The following examples and those infra are presented to help in the better understanding of the subject invention and for purposes of illustration only. They are not to be construed as limiting the invention in any manner.

EXAMPLE 1

Construction of Plasmid 19gGSE

Preparation of vector DNA. The pUC19 vector (described above) contains the lac promoter followed by the alpha-peptide coding region of beta-galactosidase. Gene fragments that are subcloned into this vector may be expressed as fusion proteins to the alpha-peptide.

The pUC19 vector plasmid was digested with EcoRI restriction enzyme and then treated with calf intestine alkaline phosphatase. An oligonucleotide adapter was synthesized to change the EcoRI overhang to an EagI overhang:

```
                 (EcoRI overhang)
GGCCGATTCG   [SEQ. ID. NO.:5]
      CTAAGCTTAA  [SEQ. ID. NO.:6]
(EagI overhang)
```

The lower oligonucleotide was kinased and then allowed to anneal with the upper oligonucleotide. The adapter was then ligated with the EcoRI digested pUC19 plasmid. After ligation, the plasmid containing the oligonucleotide adapter molecule was digested with SmaI restriction enzyme. The plasmid DNA was separated from excess oligonucleotide adapter by gel isolation on a 1% Seaplaque® agarose gel. The agarose slice containing the plasmid DNA was melted at 70° C., extracted two times with phenol, and precipitated with two volumes of 100% ethanol.

Preparation of the gG insert DNA. A plasmid containing the entire HSV-2 gG gene was obtained from D. J. McGeoch (plasmid described previously). This plasmid was digested with restriction enzymes SspI and EagI. The 1337 base pair fragment representing 92% of the gG unique sequence was gel isolated on a 1% Seaplaque agarose gel as described above. This fragment was then ligated with the pUC19 plasmid containing the oligonucleotide adapter. (The SspI and SmaI sites are compatible for ligation because both of these enzymes produce blunt ends.) The ligation produced plasmid 19gGSE, which contains a portion of the gG unique sequence fused in frame to the alpha-peptide coding region of beta-galactosidase. Expression is under the control of the lac promoter. *E. coli* strain JM103 was transformed with p19gGSE.

Preparation of *E. coli* lysates. Plasmid 19gGSE was additionally transformed into *E. coli* strain CAG456. P19gGSE was tested for expression of the gG/alpha-peptide fusion protein in both strains JM103 and CAG456. For JM103, cells were grown until A550=0.750. The promoter was then derepressed by the addition of isopropyl-beta-D-thioglacto-pyranoside (IPTG) to give a final concentration of 1 mM. Samples were taken at certain time points during the cultures growth and prepared for Western blot analysis by pelleting cells, resuspending in Laemmli buffer (62.5 mM Tris, pH 6.81, 10% glycerol, 5% beta-mercaptoethanol, 2.3% SDS) at 0.03 A550 per microliter and boiled for 10 minutes. Ten microliter samples were run on protein gels and Western blotted as described.

In CAG456, the lac promoter behaves constitutively, so that derepression with IPTG is not necessary. Cells were pelleted, resuspended in Laemmli buffer as described above for JM103, and analysed by Western blot. Lysates from both JM103 and CAG456 were tested for the presence of the recombinant gG protein in Western blot (see section below thereon for details) analysis using both HSV-2 culture confirmed patient sera and a rabbit antibody made to HSV-2 (Dako). Faint bands corresponding to 60,000 and 30,000 daltons were seen in CAG456 lysates. The theoretical molecular weight of the gG/alpha-peptide fusion protein is about 60,000 daltons. The reactivity seen at 30,000 daltons could possibly be a breakdown product.

As the level of expression appeared significantly better in CAG456, probably because of lower levels of protease therein, the fusion protein produced in that strain was selected for further purification described below in Example 3.

EXAMPLE 2

Construction of Plasmid TrpE/gG

Figure 5:
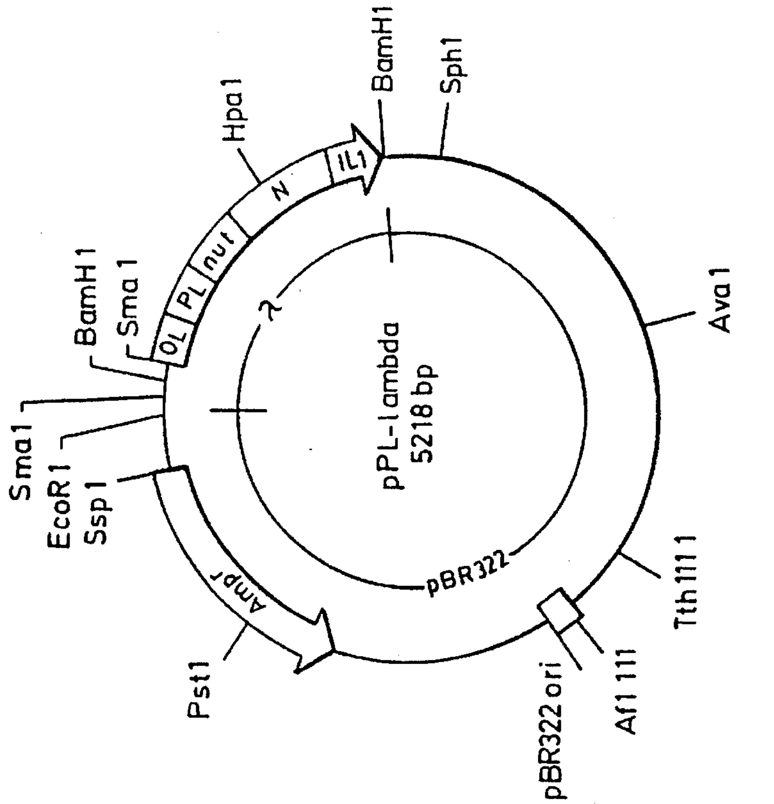
FIG. 5 is a map of expression vector pPL-lambda [obtained from Pharmacia (Piscataway, N.J.)] useful as a source material for the preparation of plasmid trpE/gG.

The pPL-Lambda inducible expression vector is a coding vector which can be purchased from Pharmacia (Piscataway, N.J.; Code No. 27-4946-01). (FIG. 5 is a diagram of that vector.) The pPL-Lambda vector contains 2 BamHI sites. It is desirable to eliminate one of the BamHI sites by deleting out a small SmaI fragment; to do so, the vector is digested with SmaI and religated, generating plasmid PLΔSma, which contains only one BamHI site.

Addition of TrpE to PLΔSma. The next step is the addition of the trpE leader sequence. The PLΔSma plasmid is first digested with SphI and then treated with $T_4$ polymerase to provide a blunt end. The plasmid is then digested with BamHI and treated with phosphatase.

The following oligo-adapter #1 containing the trpE leader is synthesized:

(trpE)

BamHI end
GATCCAGGAAATACCTTACATATGAAAGCTATCTTCGTTCTGAAAGGTTCTCTGGACCGTG-
- - - - GTCCTTTATGAATGTATACTTTCGATAGAAGCAAGACTTTCCAAGAGACCTGGCAC-
- - ACCCGGAATTCACCATGGATCCCC
blunt end [SEQ. ID. NO.:7]
- - TGGGCCTTAAGTGGTACCTAGGGG The upper strand of oligo-adapter #1 is kinased, allowed to anneal with the lower strand, and then ligated with the BamHI/blunt PLΔSma plasmid, generating a vector with two blunt ends that contains the trpE leader. The plasmid is gel isolated.

Preparation of the gG Fragment. The McGeoch plasmid containing gG (as described above in Example 1) is digested with SspI and EagI and treated with phosphatase. A 1337 base pair gG band is isolated from the gel and can be represented as follows:

SspI end ------------gG-------. EagI end
(blunt) ------------------------.

The following oligo-adapter (#2) is synthesized:

GGCCGATTCG[SEQ. ID. NO.:5]
EagI end CTAAGCTTAA[SEQ. ID. NO.:6] EcoRI end

The upper strand thereof is kinased and annealed to the lower strand. Oligo-adapter #2 is then ligated with the gG fragment, generating a gG SspI/EcoRI fragment as follows:

SspI end --------gG----------. ----oligo #2-------EcoRI end
(blunt) ----------------------. -------------------.

Preparation of the gG/α-Peptide Fusion Fragment. The plasmid pUC19 (described above in Example 1) is digested with BspHI and treated with DNA polymerase I-Klenow enzyme to effect blunt ends. The blunt-ended plasmid is treated with phosphatase and then digested with EcoRI. Isolated from the gel is a 448 base pair α-peptide fragment which is represented as follows:

α-peptide
EcoRI end --------------------. blunt end
---------------.

The α-peptide fragment is ligated with the gG SspI/EcoRI fragment, generating the following gG/α-peptide blunt fragment:

SspI end ----gG----. --oligo#2---. --α-peptide--. blunt end
(blunt) ------------. -----------. ---------.

That fragment is isolated from the gel, kinased and ligated with the blunt-ended trpE vector, generating plasmid trpE/gG. The plasmid is preferably transformed into *E. coli* strain N4830 to produce recombinantly a fused protein containing a serologically active HSV-2 gG segment. The *E. coli* N4830 strain has a lambda repressor which is heat sensitive; at higher temperatures, the repressor is deactivated, thereby derepressing the expression of the trpE/gG fused protein. In other *E. coli* strains not having such a lambda repressor, the trpE/gG protein would be produced constituitively.

Protein Purification

Example 3 is illustrative of a partial purification of the fused protein produced in accordance with Example 1.

EXAMPLE 3

Partial Purification

The *E. coli* pellet produced in accordance with Example 1 from *E. coli* strain CAG456 was resuspended in 50 mM Tris, pH 8.1, and lysozyme was added to 0.2 mg/mL. The suspension was kept on ice for one hour, then frozen at −70° C. for 2 hrs. After thawing, the lysate was brought to 2 mM $MgCl_2$ and DNase I was added to 5 μg/mL. The lysate was kept on ice for 30 minutes, then spun at 10K rpm for 30 minutes at 4° C. The pellet (Pellet 1) was resuspended by sonication in 50 mM Tris, pH 8.1, 5 mM EDTA, 5 mM EGTA containing 1% NP-40 and 1% CHAPS. The resuspended pellet was kept at room temperature for one hour, then centrifuged at 10K rpm for 30 minutes at 22° C. Pellet 2 was resuspended in 7M guanidine-HCl and dialyzed into 8M urea.

Further Purification

In order to purify the protein expressed in the host cell further, standard techniques of protein chemistry may be used. A process may be developed by first experimenting with separating the expressed fusion protein from contaminating host proteins by a series of extractions with different detergents on sample aliquots. The detergents may be from several different categories including anionic, cationic, nonionic and zwitterionic detergents. If a greater than 50/50 partition of the expressed protein and contaminating host proteins is achieved, the detergent providing the best partition may be selected as a preferred extractant. A preferred nonionic detergent for extracting the HSV-2 gG fused protein of this invention is NP-40 which was found to solubilize contaminating proteins in Pellet 2 of Example 3 above.

An evaluation of the degree of purity of the expressed protein achieved in the detergent extraction is then made. If further purification is considered desirable, a series of chaotropic extractions at different concentrations may then be tried. Preferred chaotropes include 0 to 8M urea, 0 to 7M guanidine HCl, and 0 to 4M guanidine thiocyanate (SCN). Evaluation of the effects of such chaotropic extractions on the purity of the expressed protein is then made by SDS Page (sodium dodecyl sulfate polyacrylamide gel electrophorests) and by Western blotting. The preferred chaotropes for purifying the recombinant HSV-2 gG proteins of this invention, based on their solubilizing effects on the contaminating proteins of Pellet 2 of Example 3, are 4M guanidine SCN, 7M guanidine HCl and 8M urea, wherein 8M urea is more preferred.

It is preferred that once the expressed HSV-2 gG protein has been solubilized using a chaotrope which is corrosive, viscous and/or expensive, such as guanidine SCN or guanidine HCl, that such chaotopes be removed before the next purification step, preferably by dialysis or by size exclusion chromatography.

The expressed HSV-2 gG protein may be further purified by conventional methods such as ion exchange chromatography. As many *E. coli* contaminating proteins are not charged or weakly charged at neutral pH, it is advantageous for the expressed protein of interest to have a charge at neutral pH in that such a charge differential between the expressed protein and the *E. coli* proteins allows for good separation upon an ion exchange column. If the expressed protein has a negative charge at neutral pH, anionic exchange chromatography is preferred; whereas if the expressed protein has a positive charge at neutral pH, cationic exchange chromatography is preferred. The expressed HSV-2 gG protein produced according to Example 1 has been determined to have a net charge of +5 at neutral pH. Therefore, cationic exchange chromatography is considered a preferred purification step. It would be further preferred that such cationic exchange chromatography be performed at a slightly acidic pH. Although it would be preferable not to have to use chaotropes during chromatography, if a chaotrope is necessary, urea would be a preferred chaotrope; for example the expressed fusion protein purified partially in Example 3 can remain in the 8M urea chaotrope during such chromatography.

Additional purification methods which may be useful are size fractionation using molecular sieve chromatography, affinity chromatography, using for example, antibodies directed to the expressed HSV-2 gG protein, adsorption chromatography using non-specific supports and also gel-supported electrophoresis, preferably SDS gel electrophoresis.

In developing a protein purification process, it is desirable to minimize the number of purification steps and to maximize the recovery and purification. A preferred process for purifying the expressed HSV-2 gG proteins of this invention would be initially to solubilize the contaminating proteins in the pellet with a nonionic detergent, preferably NP-40; then further extract the resulting pellet from the detergent-solubilized materials with a chaotrope, preferably 8M urea; and then use ion exchange chromatography, preferably cationic exchange chromatography.

Example 4 represents a specific procedure performed to purify a representative expressed gG protein of this invention.

EXAMPLE 4

7.5 ml of Pellet 2 in 8M urea from Example 3 above was applied to a TSK-SP-5-PW cationic exchange column (7.5×75 mm; Biorad, Hercules, Calif.). Buffer A was 25 mM $NaPO_4$ at pH 5.0; and Buffer B was 1M NaCl and 25 mM $NAPO_4$ at pH 5.0. From zero to 20 minutes, 100% of Buffer A was applied; and from 20 to 70 minutes, a 0–50% gradient of Buffer B was applied. The gG expressed protein was eluted at approximately a concentration of 35% of Buffer B.

Epitopes

When preparing proteins or polypeptides for use as immunological reagents or as vaccines, it is usually desirable that the nucleotide sequence code for a protein or polypeptide that corresponds to one or more epitopes of the natural HSV-2 gG protein. Also within the scope of this invention are synthetic and naturally produced polypeptides and proteins which contain epitopes of the HSV-2 gG protein as well as the corresponding nucleotide sequences which encode such serologically and antigenically useful polypeptide and proteins. In this regard (referring to FIG. 2), suitable polypeptides and proteins are preferably selected from the unique HSV-2 gG amino acid sequences, which include the following amino acid sequences of the HSV-2 gG unique sequence which are considered to contain one or more epitopes: from about amino acid number 45 to about amino acid number 70, from about amino acid number 95 to about amino acid number 120, from about amino acid number 165 to about amino acid 230, from about amino acid number 305 to about amino acid 330, and from about amino acid number 425 to about amino acid number 450; wherein the preferred regions are from about 45 to about 70, from about 95 to about 120, from about 305 to about 330 and from about 425 to about 450; and still more preferred are the regions from about 95 to about 120 and from about 305 to about 330. Thus, the following amino acid sequences are preferred according to this invention as are proteins and polypeptides which comprise one or more of said amino acid sequences:

H E P L G R S F L T G G L V L L A P P V
R G F G A P [SEQ. ID. NO.: 8];

Q Y G G C R G G E P P S P K T C G S Y
T Y T Y Q G G [SEQ. ID. NO.: 9];

GGE GP GP TAP P QAARAEGGP CVP P VP-AGRP WRS VPP VWYS AP NP GF RGL RF RE-RCLP P QTP AAP S D[SEQ. ID. NO.: 10];

RTGRRLMALTEDTSSDSPTSAPEKTP [SEQ. ID. NO.: 11];

and

PTSTHATPRPTTPGPQTTPPGPATPG [SEQ. ID. NO.: 12].

More preferred are the following amino acid sequences

HEPLGRSFLTGGLVLLAPPVRGFGAP [SEQ. ID. NO.: 8];

QYGGCRGGEPPSPKTCGSYTYTYQGG [SEQ. ID. NO.: 9];

RTGRRLMALTEDTSSDSPTSAPEKTP [SEQ. ID. NO.: 11];

and

PTSTHATPRPTTPGPQTTPPGPATPG [SEQ. ID. NO.: 12].

Still more preferred are the amino acid sequences:

QYGGCRGGEPPSPKTCGSYTYTYQGG [SEQ. ID. NO.: 9];

and

RTGRRLMALTEDTSSDSPTSAPEKTP [SEQ. ID. NO.: 11];

The corresponding nucleotide sequences that code for such regions are as follows, wherein the numbers used to identify such nucleotide sequences correspond to those in FIG. 1: from about nucleotide number 133 to about 210; from about 283 to about 360; from about 493 to about 690; from about 913 to about 990, and from about 1273 to about 1350; wherein the preferred sequences are those from about 133 to about 210, from about 283 to about 360, from about 913 to about 990 and from about 1273 to about 1350; and wherein the more preferred sequences are from about 283 to about 360 and from about 913 to about 990.

Synthetic and Biologic Production of HSV-2 gG Protein and Polypeptide Fragments Thereof HSV-2 gG proteins and polypeptides of this invention may be formed not only by recombinant means but also by synthetic and by other biologic means. Exemplary of other biologic means to prepare the desired polypeptide or protein is to subject to selective proteolysis a longer gG polypeptide or protein containing the desired amino acid sequence; for example, the longer polypeptide or protein can be split with chemical reagents or with enzymes. Synthetic formation of the polypeptide or protein requires chemically synthesizing the desired chain of amino acids by methods well known in the art.

The portion of a longer polypeptide or protein which contains the desired amino acids sequence can be excised by any of the following procedures:

(a) Digestion of the protein or longer polypeptide by proteolytic enzymes, specially those enzymes whose substrate specifically results in cleavage of the protein or polypeptide at sites immediately adjacent to the desired sequence of amino acids.

(b) Cleavage of the protein or polypeptide by chemical means. Particular bonds between amino acids can be cleaved by reaction with specific reagents. Examples include: bonds involving methionine are cleaved by cyanogen bromide: asparaginyl glycine bonds are cleaved by hydroxylamine; disulfide bonds between two cysteine residues are cleaved by reduction, e.g., with dithiothreitol.

(c) A combination of proteolytic and chemical changes. Of course, as indicated above, it should also be possible to clone a small portion of the DNA that codes for the synthetic peptide, resulting in the production of the peptide by the unicellular host.

The biologically or synthetically produced proteins and polypeptides once produced, may be purified by gel filtration, ion exchange or high presure liquid chromatography, or other suitable means.

Chemical synthesis of polypeptides is described in the following publications: Merrifield et al., *J. Am. Chem. Soc.*, 85:2149–2156 (1963); Kent et al., *Synthetic Peptides in Biology and Medicine*, 29 ff., eds Alitalo et al. (Elsevier Science Publishers 1985); Haug, *ABL*, 40–47 (Jan/Feb. 1987); Andrews, *Nature*, 319:429–430 (Jan. 30, 1986); Kent, *Biomedical Polymers*, 213–242, eds. Goldberg et al. (Academic Press 1980); Mitchell et al., *J. Org. Chem.*, 43: 2845:2852 (1978); Tam et al., *Tet. Letters*, 4033–4036 (1979); Mosjov et al., *J. Org. Chem.*, 45: 555–560 (1980); Tam et al. *Tet Letters*, 2851–2854 (1981); and Kent et al., *Proceedings of the IV International Symposium on Methods of Protein Sequence Analysis* (Brookhaven Press 1981).

The "Merrifield solid phase procedure" as described in the above-mentioned publications can be used to build up the appropriate sequence of L-amino acids from the carboxyl terminal amino acid to the amino terminal amino acids. Starting with the appropriate carboxyl terminal amino acid attached to an appropriate resin via chemical linkage to a chloromethyl group, benzhydrylamine group, or other reactive group of the resin, amino acids are added one by one using the following procedure for each:

(a) Peptidyl resin is washed with methylene chloride;

(b) the resin is neutralized by mixing for 10 minutes at room temperature with 5% (v/v) diisoproplethylamine (or other hindered base) in methylene chloride;

(c) the resin is washed with methylene chloride:

(d) an amount of amino acid equal to six times the molar amount of the growing peptide chain is activated by combining it with one-half as many moles of a carbodiimide, e.g. dicyclohexylcarbodiimide, diisopropylcarbodiimide, for 10 minutes at 0° C., to form the symmetric anhydride of the amino acid. The amino acid used should be provided originally as the N-α-butyloxycarbonyl derivative, with side chains protected with benzyl esters (aspartic and glutamic acids), benzyl ethers (serine, threonine, cysteine, tyrosine), benzyl oxycarbonyl groups (lysine) or other protecting groups commonly used in peptide synthesis:

(e) the activated amino acid is reacted with the peptidyl resin for 2 hours at room temperature resulting in addition of the new amino acid to the end of the growing peptide chain:

(f) the resin is washed with methylene chloride:

(g) The N-α-(butyloxycarbonyl) group is removed from the most recently added amino acid by reacting with 30% (v/v) trifluoracetic acid in methylene chloride for 30 minutes at room temperature.

(h) the resin is washed with methylene chloride;

(i) steps a through h are repeated until the required peptide sequence has been constructed. The peptide is then removed from the resin and simultaneously the side-chain protecting groups are removed, by reacting with anhydrous hydrofluoric acid containing 10% (v/v) of anisole. Subsequently, the peptide can be purified by gel filtration, ion exchange, or high pressure liquid chromatography, or other suitable means.

Chemical synthesis can be carried out without a solid phase resin, in which case the synthetic reactions are performed entirely in solution. The reactions, and the final product, are otherwise essentially identical.

Techniques of chemical peptide synthesis include using automatic peptide synthesizers, employing commercially available protected amino acids; such synthesizers include, for example, Biosearch (San Rafael, Calif.) Models 9500 and 9600, Applied Biosystems Inc. (Foster City, Calif.) Model 430, and MilliGen (a division of Millipore Corp.) Model 9050. Further, one can manually synthesize up to about 25 polypeptides at a time by using Dupont's Ramp (Rapid Automated Multiple Peptide Syntheis).

The synthetic polypeptides according to this invention preferably comprise one or more epitopes of the HSV-2 unique sequence gG, preferably as indicated above. It is possible to synthesize such polypeptides by attaching the amino acid sequence which defines an epitope (which can be from about three to about eight amino acids, more usually from .about five to about eight amino acids) to at least three amino acids flanking either side thereof. The three amino acids on either side can be the same amino acids as in the natural unique gG sequence or could be other amino acids.

Testing for Serological Activity

Immunoblot Procedure. Serological reactivity of the recombinant gG protein, prepared according to Example 1 and partially purified according to Example 3 was evaluated by Western immunoblot assay.

General background on the Western immunoblot assay technique can be found in: Towbin, et al., *PNAS (USA)*, 76:4350 (1979); Towbin et al., U.S. Pat. No. 4,452,901 (Jun. 5, 1984); Towbin, et al., *J. Immunol. Methods*, 72(2):313 (1984); and Bittner et al., *Anal. Biochem.*, 102:459, (1980).

The specific procedure outlined below in Example 5 was used to test the recombinant unique sequence gG protein produced according to this invention. The protein was reactive with rabbit HSV-2 antiserum but not with rabbit HSV-1 antiserum. [The rabbit antisera were purchased from Dako.] In addition, the recombinant gG protein reacted with a HSV-2 gG monoclonal antibody obtained from N. Balachandran (University of Florida, Gainesville, Fla.). That anti-HSV-2 monoclonal antibody is described in Balachandran et al., *J. Virol.*, 44: 344–355 (1982).

Patient sera tested by immunoblot according to Example 5 (the results for which are recorded in Table 2) were obtained from L. M. Frenkel (UCLA School of Medicine; Los Angeles, Calif.), C. Probet (Stanford University; Palo Alto, Calif.), from J. Kettering (Loma Linda Medical Center, Loma Linda, Calif.) and Biomedical Resources (Pa.).

Thirty-seven out of 39 patient sera known to have antibody to HSV-2 established by virus isolation, clinical history or by positive reactivity with native, glycosylated, full-length gG as assayed by Sullender et al., supra were reactive in the immunoblot assay with the partially purified recombinant, nonglycosylated, unique sequence gG protein of this invention. None of the 19 patient sera that had only prior HSV-1 infection as established by clinical history or absence of antibody reactivity with native HSV-2 gG as assayed by Sullender et al., id showed reactivity in the immunoblot assay. None of the eight patient sera which were established to be free of either HSV-1 or HSV-2 antibodies showed reactivity in the immunoblot assay.

Paired acute and convalescent sera from four patients similarly tested by immunoblot according to Example 5 (the results for which are recorded in Table 3) were obtained from the Department of Health Services—Health Protection Division of Berkeley, Calif. Table 3 indicates that the representative unique gG sequence protein of this invention, partially purified according to Example 3, is useful in an immunoblot assay to diagnose whether a patient has had active HSV-2 infection. The darkness of the band on the Western blot indicating reactivity of a patient's antibodies to the unique sequence gG protein is directly proportional to the patient's antibody titer. An increase in antibody titer from that in a patient's acute serum sample to that in the same patient's convalescent serum sample (taken 10 days later) is indicative of an active infection of HSV-2. Table 3 indicates that all of the paired serum samples of the three patients, who had been confirmed as having HSV-2 by viral isolation and typing, were positive in the representative serological assay of this invention; further, the titer rise shown from the acute to the convalescent samples indicated that all three patients had active infections. Both of the paired sera samples of the one patient, who had been confirmed to have a HSV-1 infection, registered negative in the assay.

An advantage of the recombinant unique sequence gG of this invention over the native gG of the Sullender et al. assay is its lack of epitopes to HSV-1. That advantage was demonstrated by the lack of reactivity the recombinant gG had with anti-HSV-1 rabbit polyclonal antibody and antibody from HSV-1 infected only patient sera. Thus, the cross-reactivity problem of the Sullender et al. assay using native, glycosylated, full-length gG in differentiating between HSV-1 and HSV-2 antibodies, especially wherein antibodies to both serotypes are present in patient sera, is obviated by the use of the recombinant unique sequence gG proteins and polypeptides of this invention. An additional advantage of the recombinant gG is that it is much cheaper to produce than the native gG.

EXAMPLE 5

Immunoblot procedure

Pellet 2 of Example 3 was electrophoresed on 8% polyacrylamide slab gels in the presence of SDS using the procedure of Laemmli. Proteins were electrophoretically transferred onto nitrocellulose for 60 minutes at 200 mA using transfer buffer composed of 25 mM Tris-HCl, 192 mM glycine, and 20% methanol. The nitrocellulose was blocked for 20 minutes in 1M glycine, 5% (w/v) nonfat dry milk, and 1% (w/v) ovalbumin, and was then incubated with sera diluted 1/75 in blocking buffer at 4 degrees C. overnight. After three 3-minute rinses in PBST, the nitrocellulose was incubated with HRP-labeled goat anti-human IgG in 10% FBS in PBST for 2 hours at room temperature. The nitrocellulose was again rinsed and developed in substrate-chromogene solution containing 0.2 mg/mL 3,3'-diaminobenzidine –4HCl, 0.02% (w/v) $NiCl_2$, and 0.05% (w/v) $H_2O_2$ in 10 mM Tris-HCl, pH 7.5. The reaction was stopped by rinsing the nitrocellulose in water. The results of such assays are summarized in Tables 2 and 3 below.

TABLE 2

Table 2. Serological reactivity of recombinant HSV-2-specific gG with patient sera.

| Patient Group | No. of Patients | % Positive[a] |
|---|---|---|
| Prior HSV-2 infection[b] | 39 | 95% |
| Prior HSV-1 Only[c] | 19 | 0% |
| No Prior HSV-1 or HSV-2[d] | 8 | 0% |

[a]Positive reactivity determined by immunoblot assay using partially purified recombinant HSV-2-specific gG.
[b]Prior HSV-2 infections established by virus isolation, clinical history or by positive reactivity with native HSV-2 gG as assayed by Sullender et al., supra.
[c]Prior HSV-1 infection only established by clinical history or absence of antibody reactivity with native HSV-2 gG as assayed by Sullender et al., supra.
[d]No prior HSV-1 or HSV-2 infection established by the absence of HSV-1 or HSV-2 antibodies. (Plummer et al., supra.)

TABLE 3

Detection of recombinant HSV-2-specific gG antibody in acute/convalescent serum pairs.

| Type of HSV-2 Infection[a] | No. of Patients with Paired Samples | Acute Sera Samples[b] | Convalescent Samples[b] | Titer Rise[c] |
|---|---|---|---|---|
| HSV-2 | 3 | all 3 either positive or weakly positive | all 3 strongly positive | Yes |
| HSV-1 | 1 | negative | negative | No |

[a]The type of HSV infection was determined by the isolation and typing the virus from the patients' lesions.
[b]An acute serum specimens was drawn from the patients at the time of their first visit to the clinician. A second serum sample (the convalescent sample) was drawn ten days later.
[c]Demonstration of a rise in antibody levels to recombinant HSV-2-specific gG was done by immunoblot assay.

Diagnostic Tests for HSV-2

It is clear that the unique sequence HSV-2 gG proteins and polypeptides of the instant invention may be used as diagnostic reagents for the detection of HSV-2 type-specific antibodies. Polypeptides or proteins displaying unique sequence HSV-2 gG antigenicity and the DNA sequences which code therefor may be used in methods and kits designed to detect the presence of type-specific antibodies in humans and therefore recognize humans which have been infected by this virus.

For example, the unique sequence gG proteins and polypeptides produced by hosts transformed by recombinant DNA molecules of this invention can be used in the formats of the immunological diagnostic tests currently available, that is, radioimmunoassay or ELISA (enzyme linked immunosorbent assay).

Preferably in one type of ELISA test, a microtiter plate is coated with unique sequence gG protein/polypeptide and to this is added a sample of patient's serum. After a period of incubation permitting any antibody to bind to the antigen, the plate is washed and a preparation of anti-human antibodies, raised in a laboratory animal, and which are linked to an enzyme is added, incubated to allow reaction to take place, and the plate is then rewashed. Thereafter, enzyme substrate is added to the microtiter plate and incubated for a period of time to allow the enzyme to work on the substrate, and the adsorbance of the final preparation is measured. A large change in absorbance indicates a positive result.

It is also apparent to one of ordinary skill that a diagnostic assay for HSV-2 using polyclonal or monoclonal antibodies to the HSV-2 unique sequence gG proteins and polypeptides of the instant invention may be used to detect the presence of HSV-2. In one embodiment a competition immunoassay is used wherein the antigenic substance, in this case HSV-2, in a vesicle sample competes with a known quantity of labelled antigen, in this case labelled unique sequence HSV-2 gG proteins and polypeptides, for a limited quantity of antibody binding sites. Thus, the amount of labelled antigen bound to the antibody is inversely proportional to the amount of antigen in the sample. In another embodiment, an immunometric assay may be used wherein a labelled antibody to a HSV-2 unique sequence protein or polypeptide is used. In such an assay, the amount of labelled antibody which complexes with the antigen-bound antibody is directly proportional to the amount of antigen (HSV-2) in the vesicle sample. In a simple yes/no assay to determine whether HSV-2 is present in vesicle specimens, the solid support is tested to detect the presence of labelled antibody. In another embodiment, monoclonal antibodies to the HSV-2 unique sequence gG proteins or polypeptides may be used in an immunometric assay. Such monoclonal antibodies may be obtained by methods well known in the art, particularly the process of Kohler and Milstein reported in *Nature,* 256:495–497 (1975). Example 6, immediately below is representative of such an immunometric assay.

EXAMPLE 6

Immunometric Assay for HSV-2

Rabbit polyclonal antibody produced against HSV-2 unique sequence gG protein and/or polypeptides is prepared. Duplicate samples are run in which 100 ul of a suspension of such antibody immobilized on agarose particles is mixed with 100 ul of serum and 100 ul of soluble $^{125}$I-labelled antibody produced against HSV-2 unique sequence protein and/or polypeptide. This mixture is allowed to incubate for specified times ranging from one quarter hour to twenty-four hours. Following the incubation period, the agarose particles are washed by addition of buffer and then centrifuged. After removal of the washing liquid by aspiration, the resulting pellet of agarose particles is then counted for bound $^{125}$I-labelled antibody. The counts obtained for each of the complexes can then be compared to the control sample.

Such diagnostic methods can be embodied in test kits to assay for HSV-2 type-specific antibodies in human bodily fluids wherein such test kits can comprise (a) a solid phase coated with recombinantly produced nonglycosylated or glycosylated proteins encoded by the unique sequence of HSV-2 gG or fragments thereof or with synthetically produced polypeptides that have the same or substantially the same amino acid sequence as those encoded by the unique sequence of HSV-2 gG or portions thereof or biologically produced gG unique sequence polypeptide and/or proteins; and (b) a detection means. Test kits designed to detect HSV-2 itself can further comprise antibodies, preferably monoclonal antibodies, to the HSV-2 unique sequence proteins/polypeptides.

Suitable detection means include the use of labels such as radionuclides, enzymes, fluorescers, chemiluminescers, enzyme substrates or co-factors, enzyme inhibitors, particles, dyes and the like. Such labeled reagents may be used in a variety of well known assays, such as radioimmunoassays, enzyme immunoassays, e.g., ELISA, fluorescent immunoassays, and the like. See, for example, U.S. Pat. Nos. 3,766,162; 3,791,932; 3,817,837; and 4,233,402.

Antibodies to gG

Antibodies to the recombinant, synthetic or natural HSV-2 gG proteins and polypeptides, preferably to the recombinant, synthetic or natural unique sequence gG proteins/polypeptides of this invention, have use not only for diagnostic assays but also for affinity purification of gG proteins/polypeptides and for therapeutic use by procedures of passive immunization. When the antibodies are used therapeutically for passive immunization or in diagnostic assays, it is preferred that they be to the unique sequence gG proteins/polypeptides of this invention.

Vaccines

As indicated above and shown in Table 2, 95% of the tissue culture confirmed HSV-2 positive sera contained antibodies to the representative unique specific recombinant gG protein of this invention. This data strongly suggest that the HSV-2 unique sequence gG proteins and polypeptides of this invention would be immunogenic in humans.

An advantage of using unique sequence gG proteins and/or polypeptides as vaccines against HSV-2 resides in their demonstrated lack of cross-reactivity with antibodies to HSV-1. More people have been exposed to HSV-1 than HSV-2, and a substantial number of people have antibodies to HSV-1. Adverse reactions may occur upon the introduction of a vaccine for HSV-2, such as full-length glycosylated gG, which has epitopes that are not unique to HSV-2 and which may react with the pre-existing HSV-1 antibodies. Such adverse reactions, for example, vaccine reactions such as immune complex diseases or anaphylactic shock, are not anticipated as a problem wherein unique sequence gG proteins and/or polypeptides are employed as vaccines in that they are not cross-reactive with antibodies to HSV-1.

It will be readily appreciated that the HSV-2 unique sequence gG proteins and polypeptides of this invention can be incorporated into vaccines capable of inducing protective immunity against HSV-2. Preferably, said HSV-2 unique sequence gG proteins and polypeptides are those containing the amino acid sequences noted above as encompassing epitopes of the unique sequence. Polypeptides may be-synthesized or prepared recombinantly or otherwise biologically, to comprise one or more amino acid sequences corresponding to one or more epitopes of the HSV-2 unique sequence gG either in monomeric or multimeric form. These polypeptides may then be incorporated into vaccines capable of inducing protective immunity against HSV-2. Techniques for enhancing the antigenicity of such polypeptides include incorporation into a multimeric structure, binding to a highly immunogenic protein carrier, for example, keyhole limpet hemocyanin (KLH), or diphtheria toxoid, and administration in combination with adjuvants or any other enhancers of immune response. In addition, the vaccine composition may comprise antigens to provide immunity against other diseases in addition to HSV-2.

An amino acid sequence corresponding to an epitope of HSV-2 unique sequence gG either in monomeric or multimeric form may be obtained by chemical synthetic means or by purification from biological sources including genetically modified microorganisms or their culture media. [See Lerner, "Synthetic Vaccines", *Sci. Am.* 248(2):66–74 (1983).] The polypeptide may be combined in an amino acid sequence with other polypeptides including fragments of other proteins, as for example, when synthesized as a fusion protein, or linked to other antibenic or non-antigenic polypeptides of synthetic or biological origin.

The term "corresponding to an epitope of a HSV-2 unique sequence gG" will be understood to include the practical possibility that, in some instances, amino acid sequence variations of naturally occurring protein and polypeptide may be antigenic and confer protective immunity against HSV-2. Possible sequence variations include, without limitation, amino acid substitutions, extensions, deletions, interpolations and combinations thereof. Such variations fall within the contemplated scope of the invention provided the protein or polypeptide containing them is antigenic and antibodies elicited by such polypeptide or protein cross-react with naturally occurring HSV-2 unique sequence gG proteins and polypeptides to an extent sufficient to provide protective immunity when administered as a vaccine.

Such vaccine compositions will be combined with a physiologically acceptable medium, including immunologically acceptable diluents and carriers as well as commonly employed adjuvants such as Freund's Complete Adjuvant, saponin, alum, and the like. Administration would be in immunologically effective amounts of the HSV-2 unique sequence gG proteins or polypeptides, preferably in quantities providing unit does of from 0.01 to 10.0 micrograms of immunologically active unique sequence gG protein or polypeptide per kilogram of the recipient's body weight. Total protective doses may range from 0.1 to about 100 micrograms of antigen.

Routes of administration, antigen dose, number and frequency of injections are all matters of optimization within the scope of ordinary skill in the art particularly in view of the fact that there is experience in the art in providing protective immunity by the injection of other related antigens to provide immunity in other viral infections. [See Wise et al., "Herpes Simplex Virus Vaccines" *J. Inf. Dis.*, 136:706–711 (1977).] It is anticipated that the principal value of providing immunity to HSV-2 infection will be for those individuals who have had no previous exposure to HSV-2. It is also anticipated that temporary immunity for infants may be provided by immunization of mothers during pregnancy.

DNA Probes

The unique sequence of HSV-2 gG and fragments thereof are useful as DNA probes which are specific for HSV-2. Said DNA probes are at least 14 nucleotides long and usually from about 20 to about 70 nucleotides in length. Specific examples of DNA probes from the unique sequence of HSV-2 gG include the nucleic acid sequence from about nucleotide 45 to about nucleotide 1386 of FIGS. 1A and 1B (cloned according to Example 1) and more preferably fragments thereof. Said DNA probes are purified and isolated from contaminating materials according to methods well known in the art.

Conclusion

This invention provides for rapid diagnostic tests that are currently needed by clinicians, especially by obstetricians, to diagnose both asymptomatic and symptomatic HSV-2 infections. It may be seen, further, that the recombinantly, synthetically or biologically produced proteins and polypeptides provided by this invention can serve not only as diagnostic reagents but also as the basis for vaccines to protect against HSV-2. The invention still further provides for antibodies that can be used both therapeutically and diagnostically in regard to HSV-2 infections. Still further, this invention provides for DNA probes specific for HSV-2 DNA.

It is understood that the hybrid micro-organisms, recombinant DNA molecules and proteins/polypeptides and methods applicable to them of this invention are not limited to those described in the preferred embodiments above. The hybrid organisms, recombinant DNA molecules and protein/polypeptides may be modified during production or subsequently by known methods to good advantage. For example, more efficient control sequences may be used for transcription of the HSV-2 gG sequences, mutations to reduce the synthesis of undesired products may be introduced, the protease levels in the host cells may be reduced, thermo-inducible lysogens containing the HSV-2 gG sequences may be integrated into the host chromosome or other modifications and procedures may be carried out to increase the number of sequence copies in the cell or to increase the cell's productivity in producing the desired protein/polypeptide.

Various modifications of the invention in addition to those shown and described herein will become apparent to those in the art from the foregoing description. Such modifications are intended to be within the scope of the appended claims.

---

What we claim is:

1. A recombinant DNA molecule comprising a HSV gG2 nucleotide sequence encoding an amino acid sequence consisting of SEQ ID NO: 4, wherein the only gG2 nucleotide sequence present is that which encodes the polypeptide of SEQ ID NO: 4.

2. The recombinant DNA molecule of claim 1 wherein the nucleotide sequence consists of SEQ ID NO: 3.

3. A unicellular host which is either prokaryotic or eukaryotic which is transformed with the recombinant DNA molecule of claim 1.

4. The unicellular host according to claim 2 wherein the recombinant DNA molecule is a recombinant cloning vehicle comprising a first and second restriction endonuclease recognition site, said DNA sequence being inserted between said first and second restriction sites.

5. The unicellular host according to claim 3 wherein said host is *E. coli*, Pseudomonas, Bacillus yeast, fungi, an animal cell, an insect cell, or a plant cell.

6. The unicellular host according to claim 5 which is an *E. coli* strain.

7. A method for producing the unique sequence HSV-2 glycoprotein G protein comprising the steps of:

(a) transforming a unicellular host with a recombinant DNA molecule of claim 1, (b) culturing said transformed host so that said unique sequence HSV-2 glycoprotein G protein is expressed; and (c) extracting and isolating said unique sequence HSV-2 glycoprotein G protein.

8. A recombinant DNA molecule comprising a sequence which encodes a fragment of the unique sequence HSV-2 glycoprotein G protein, wherein said sequence is selected from the group consisting of nucleotide 133 to 210, 283 to 360, 493 to 690, 913 to 990, and 1273 to 1350 of SEQ ID NO: 1, wherein said sequence is operatively linked to an expression control sequence in said DNA molecule.

9. The recombinant DNA molecule according to claim 8 wherein said nucleotide sequence is 133 to 210, 283 to 360, 913 to 990 or 1273 to 1350 of SEQ ID NO: 1.

10. The recombinant DNA molecule according to claim 9 wherein said nucleotide sequence is 283 to 360 or 913 to 990 of SEQ ID NO: 1.

11. A unicellular host which is either prokaryotic or eukaryotic which is transformed with the recombinant DNA molecule of claim 8.

12. The unicellular host according to claim 11 wherein the recombinant DNA molecule is a recombinant cloning vehicle comprising a first and second restriction endonuclease recognition site, said DNA sequence being inserted between said first and second restriction sites.

13. The unicellular host according to claim 11 wherein said host is *E. coli*, Pseudomonas, Bacillus, yeast, fungi, an animal cell, an insect cell, or a plant cell.

14. The unicellular host according to claim 13 which is an *E. coli* strain.

15. A method for producing a fragment of the unique sequence HSV-2 glycoprotein G protein comprising the steps of:

(a) transforming a unicellular host with a recombinant DNA molecule of claim 8;

(b) culturing said transformed host so that said unique sequence HSV-2 glycoprotein G protein is expressed; and (c) extracting and isolating said unique sequence HSV-2 glycoprotein G protein.

16. A purified and isolated DNA molecule which codes for the unique sequence HSV-2 glycoprotein G protein which has the amino acid sequence from amino acid 16 to 462 designated as SEQ. ID. No. 4, wherein said DNA consists of the nucleotide sequence designated as SEQ. ID. No. 3.

17. A purified and isolated DNA molecule which codes for a fragment of the unique sequence HSV-2 glycoprotein G protein selected from the group consisting of nucleotide 133 to 210, 283 to 360, 493 to 690, 913 to 990, and 1273 to 1350 of SEQ ID NO: 1.

* * * * *